(12) United States Patent
Heinonen et al.

(10) Patent No.: US 8,669,112 B2
(45) Date of Patent: Mar. 11, 2014

(54) AUTOMATED INSTRUMENTATION AND METHOD FOR MEASUREMENTS OF SAMPLES

(75) Inventors: Aarne Heinonen, Turku (FI); Juha Karunen, Littoinen (FI); Jarmo Korpi, Nousiainen (FI); Jarmo Nurmi, Kuusisto (FI); Markku Ojala, Turku (FI); Timo Salminen, Turku (FI); Paul White, New South Wales (AU)

(73) Assignee: Wallac Oy, Turku (FI)

( * ) Notice: Subject to any disclaimer, the term of this patent is extended or adjusted under 35 U.S.C. 154(b) by 841 days.

(21) Appl. No.: 12/664,331

(22) PCT Filed: Jun. 12, 2008

(86) PCT No.: PCT/FI2008/050350
§ 371 (c)(1),
(2), (4) Date: Apr. 20, 2010

(87) PCT Pub. No.: WO2008/152204
PCT Pub. Date: Dec. 18, 2008

(65) Prior Publication Data
US 2010/0203573 A1    Aug. 12, 2010

Related U.S. Application Data

(60) Provisional application No. 60/943,393, filed on Jun. 12, 2007.

(30) Foreign Application Priority Data

Jun. 12, 2007  (FI) ...................................... 20075439

(51) Int. Cl.
*G01N 35/00*    (2006.01)

(52) U.S. Cl.
USPC .................................. 436/43; 422/63; 422/64

(58) Field of Classification Search
USPC ....................................................... 422/63, 64
See application file for complete search history.

(56) References Cited

U.S. PATENT DOCUMENTS

| 5,474,742 A * | 12/1995 | Tuuminen ....................... 422/63 |
| 5,955,373 A   | 9/1999  | Hutchins et al. |
| 6,323,035 B1  | 11/2001 | Kedar et al. |

(Continued)

FOREIGN PATENT DOCUMENTS

| EP | 1 582 874 A1 | 10/2005 |
| WO | 98/53301 A2  | 11/1998 |
| WO | 99/15905 A1  | 4/1999 |
| WO | 01/57539 A1  | 8/2001 |

*Primary Examiner* — Jill Warden
(74) *Attorney, Agent, or Firm* — Sughrue Mion, PLLC

(57) ABSTRACT

Instrumentation and a method for efficient and reliable assaying and measuring samples. The teachings include an automated self-contained instrument, wherein the samples are located on wells of sample plates, and the instrument includes a plurality of units for processing or storing sample plates. The instrument may includes at least one dispensing unit for dispensing reagents or other assay components to the sample wells, at least two units for simultaneously processing or storing a plurality of sample plates, at least one unit for removing substance from the sample wells, and one or several measurement units for optically measuring samples in at least two measurement modes. Further, the instrument includes a manipulator for moving the sample plates in three orthogonal directions or combinations thereof and for rotating the sample plates in relation to a vertical axis for transferring the sample plates to the units.

14 Claims, 11 Drawing Sheets

(56) References Cited

U.S. PATENT DOCUMENTS

| | | |
|---|---|---|
| 6,325,114 B1 | 12/2001 | Bevirt et al. |
| 6,649,128 B1 | 11/2003 | Meyer et al. |
| 6,746,864 B1 | 6/2004 | McNeil et al. |
| 2002/0012611 A1 | 1/2002 | Stylli et al. |
| 2003/0215357 A1 | 11/2003 | Malterer et al. |
| 2004/0053414 A1 | 3/2004 | Devlin, Sr. |
| 2004/0089330 A1 | 5/2004 | Muller |
| 2006/0083660 A1 | 4/2006 | Schorno et al. |
| 2006/0210435 A1 | 9/2006 | Alavie et al. |
| 2007/0004028 A1 | 1/2007 | Lair et al. |
| 2007/0053798 A1 | 3/2007 | Johnson et al. |
| 2007/0123999 A1 | 5/2007 | Raghibizadeh et al. |

\* cited by examiner

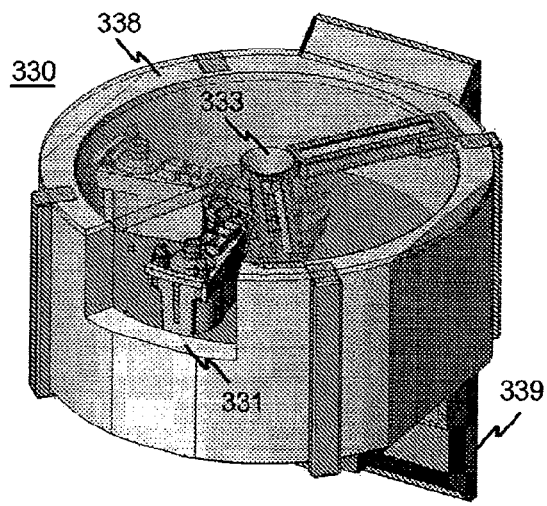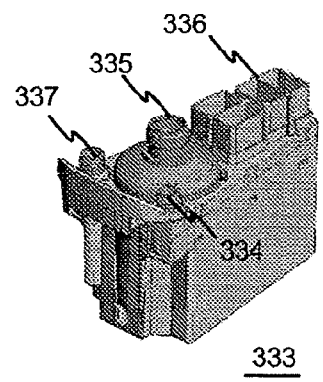
Fig. 3a  Fig. 3b
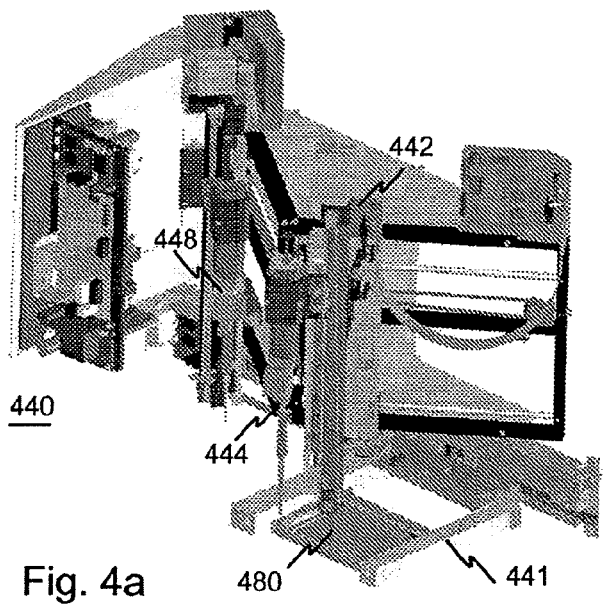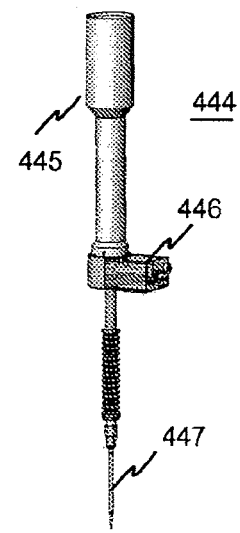
Fig. 4a  Fig. 4b

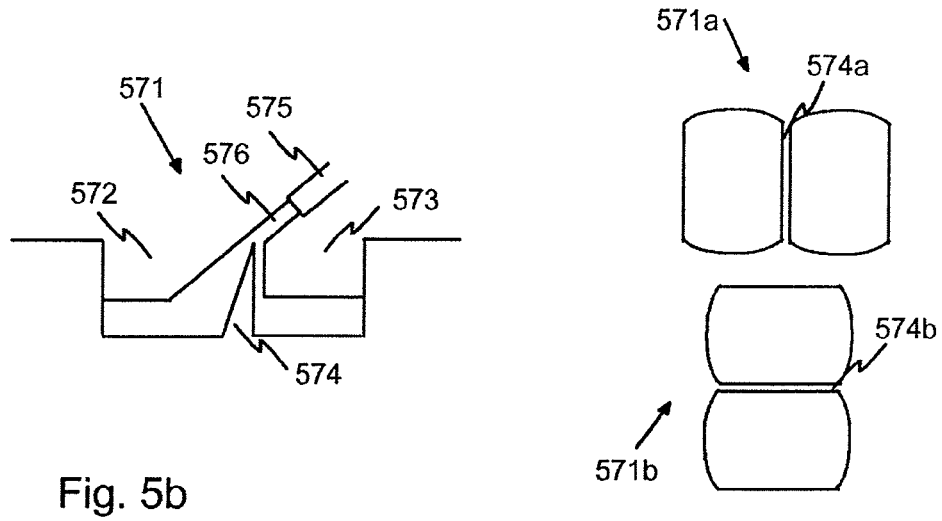
Fig. 5b
Fig. 5c
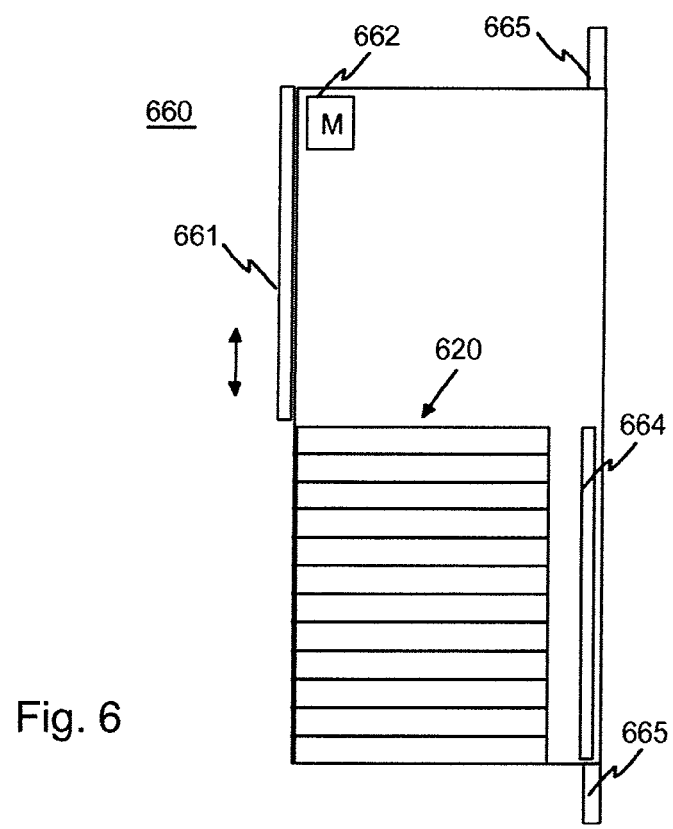
Fig. 6

US 8,669,112 B2

AUTOMATED INSTRUMENTATION AND METHOD FOR MEASUREMENTS OF SAMPLES

CROSS REFERENCE TO RELATED APPLICATIONS

This application is a National Stage of International Application No. PCT/FI2008/050350 filed Jun. 12, 2008, claiming priority based on U.S. Provisional Application No. 60/943,393 filed Jun. 12, 2007 and Finland Patent Application No. 20075439 filed Jun. 12, 2007, the contents of all of which are incorporated herein by reference in their entirety.

TECHNICAL FIELD

The present teachings relate generally to the field of biochemical laboratory instrumentation for measuring compounds in samples using microtitration plates or corresponding sample supports.

BACKGROUND

The routine diagnostics and research in analytical, clinical and biochemical laboratories is often based on biochemical assay methods using different tags or labels coupled to specific reagents allowing sensitive and specific determination of desired compounds in the samples. The typical labels e.g. in immunoassays are different radioactive isotopes, enzymes, different luminescent and fluorescent molecules, for example those of chelates of rare earth metals.

The detection of the analyte can be done directly based on the label, or indirectly, as is done for example in enzymatic assays and in immunoassays. Enzyme immunoassays (ELISA) are often based on enzyme substrate molecules labelled with a reporter group, which upon enzymatic reaction is turned into light absorbing compound, i.e. its absorbance properties are changed upon enzymatic reaction in respect of absorbance wavelength or molar absorptivity. Alternatively enzyme activity can be measured using fluorogenic or luminogenic substrates which upon enzymatic reaction form highly fluorescent, or luminescent respectively, end products. Respectively enzymes as such can be quantitated in the samples using similar substrates. The enzymatic activity is subsequently monitored either kinetically or by end-point detection with a suitable photometer, fluorometer in case of fluorogenic substrates are used, or luminometer if luminogenic substrate are used.

Fluorometric detection is used in various assays based on fluorescent labels or fluorogenic substrates. Fluorometric detection with a fluorometry is based on excitation of the label by excitation light, and detection of the relaxation process of the molecule by its emission which generally takes place at a longer wavelength. In prompt photoluminescence (FI) the emission signal is measured simultaneously and/or immediately after excitation. In time-resolved fluorometry (TRF), the signal acquisition window starts after a determined delay from the excitation pulse. This way quickly decaying emission signals from other sources will have less disturbing effects. Typically TRF measurements are applied with labels with relatively long photoluminescence life-time, for example with chelates of rare earth metals having decay time in the range from microseconds to milliseconds.

A further commonly used measurement method is chemiluminescence measurement where the label is excited by a chemical reaction, and emission of the label molecule is measured from a sample without prior illumination.

A typical instrument in research, biochemistry, screening or in clinical laboratory is microtitration plate based filter photometer, fluorometer or luminometer. The instrument may also be multipurpose reader able to measure different labels, or it may be composed of monochromators.

A measurement instrument may comprise only a measurement unit for providing the optical measurement, and a control unit 70 controlling the measurement and processing detected signals. In such a case the other steps of the assay or sample pre-treatment must be performed separately. These assay steps may include sample pre-treatment, partial purification, dilution, filtrations, elution, pre-incubation with required reagents, intermediate and final washings, shakings, incubations and so on. In heterogeneous specific binding assays the added reagents which may contain excess of labels are generally washed before signal development and/or detection. If it is desired to make measurements with different measuring methods, the sample handling must be performed separately for each kind of measurement. Also, it may be necessary to use different types of measurement instruments for different measurement modes.

There are also automated analysing instruments which perform all or part of the assaying steps automatically within the instrument. Next an exemplary automated instrument is briefly discussed.

FIG. 1 illustrates an instrumentation where samples are assayed automatically. FIG. 1 shows schematically a side view of a measuring apparatus 10 and a sample dispenser 20, which is connected to it. The main parts of the measuring apparatus 10 are a shaker/incubator 30 also functioning as the store of sample plates, a reagent cassette 24 and a measurement head 50. Inside the measuring apparatus 10, there are also various sample handling devices 13-18. A conveyor 12 and an elevator 31 are used for transferring a sample plate 11.

Empty sample plates 11 are first loaded into the measuring apparatus 10. This is performed by feeding the sample plates one by one on the conveyor 12 at that end of the apparatus which is situated by the sample dispenser 20 on the left side of FIG. 1. The conveyor 12 transfers the sample plate 11 to the elevator 31 which lifts the sample plate 11 into the shaker/incubator 30. Before the actual operation of the measuring apparatus 10, reagent boxes 26 needed in the measurement must be loaded in the reagent cassette 24 of the measuring apparatus 10.

When the measuring apparatus 10 is actuated, the elevator 31 and the conveyor 12 fetch the first sample plate 11 from the shaker/incubator 30, which functions as a store of sample plates, and convey it in front of the washer 13. The valve 14 of the washer 13 dispenses washing liquid from a container outside the measuring apparatus 10 to the sample plate 11 under a pipetting apparatus 41. The pipetting apparatus 41 fetches an unused pipette tip 28 and dispenses the reagent material from a reagent bottle 45 in the reagent cassette 24 on the sample plate 11.

The sample plate 11 with the reagent material is then transferred to the shaker/incubator 30 which performs shaking and simultaneous incubation. Then the elevator 31 transfers the sample plate 11 back on to the conveyor 12 whereby the sample plate 11 is again transferred under the washer 13. After washing, the sample plate 11 is carried under a measuring liquid dispenser 17 where a pump 18 of the measuring liquid dispenser 17 dispenses measuring liquid into the wells of the sample plate 11 from a bottle 19. The sample plate 11 is then again conveyed to the shaker/incubator 30 where a shaking is performed. After shaking, the sample plate is transferred to the measurement unit 50 for measurement. After the measurement, the sample plate 11 is transferred back to the shaker/incubator 30 which functions as the store of the sample plates 11. The sample plate is finally transferred with the elevator and the conveyor to an unloading position.

Measurement instruments are increasingly used for screening purposes. One example of screening is neonatal screening in which blood spots of newborn babies are measured. The blood spots are generally impregnated into a filter paper, and small discs are punched from the filter paper as samples to be measured.

In screening applications the number of samples is large and therefore high efficiency of assaying and measurements of the samples are required. Also, it is often required to perform different kinds of assays with possibly different chemistries, and use different kinds of measurement modes in the optical measurements. The large numbers of samples need to be measured with high accuracy and reliability.

The known automated instruments are capable of processing several sample plates simultaneously. However, it is generally not possible to have different kinds of assays with possibly different chemistries simultaneously processed in those instruments. For example, a conveyor belt commonly used for transferring the sample plates can transfer only one sample plate in only one direction at a time. A sample plate is also located on the conveyor during the processing of phases of the sample plate. It is not possible to move any other sample plates during the processing of one sample plate situated on the conveyor. Also, the sample plates need to be conveyed relatively long distances inside the instrument. For example, when a certain unit has finished processing a sample plate, it takes time to transfer the processed plate to the storage and to transfer a next, unprocessed plate, to the processing unit. And during the transfer, it is not possible to utilise the processing units which are located by the conveyor. This increases the required overall processing times. Therefore the known automated instruments are practically limited to performing one type of assay successively at any time.

The different kinds of assays need different kinds of processing. For example, the phases of shaking incubation, non-shaking incubation, high temperature incubation, room temperature incubation and dispensing of different kinds of reagents need to be done in different succession in different types of assays. Therefore, it is difficult if not impossible to perform assays of different types possibly including different chemistries simultaneously in an automated instrument.

The known automated instruments do not provide all functions required for different kinds of assays. For example, different types of assays require different temperatures of wash solution. However, the automated systems generally have constant washing procedures which may not be suitable or at least optimized for all types of measurements. It is also difficult to update new functions to the known instruments because the instruments have no required space or required interfaces for additional functional units.

Further, in many screening purposes it is necessary to perform the optical measurement of samples with different measurement modes, such as prompt photoluminescence, time-resolved fluorometry, chemiluminescence and absorbance measurement modes. However, since the known automated instruments are practically limited to simultaneously performing only one type of assays, they generally also have a capability for only one mode of optical measurements.

For the above reasons it is necessary to have a multitude of equipment for efficiently measuring large numbers of samples with different kinds of assaying, chemistries and measurement modes.

There are also some other disadvantages related to the prior art instruments. The instruments must generally be in a standby state when reagent containers are filled or changed or when sample plates are loaded/unloaded. This means that the user must wait for a suitable phase in the processes of the instrument until those procedures of filling/changing/loading/unloading are possible. This also concerns the filling of a washing solution container and emptying of a waste tank of the instrument. A user thus needs to plan the work schedule according to the schedules of the instrument. And these servicing functions also tend to take much user's time and the processing time of the instrument. Preparing, transferring and handling of large containers of washing liquid and waste tanks also includes much manual work in a laboratory.

One further disadvantage of the known instruments is that they tend to require much space on the laboratory floor because of the large number of successive processing units within the instrument. This is especially a problem is several instruments are needed for performing different kinds of measurements of for achieving the required efficiency.

An automated system for effective screening must function in a reliable manner. Even short periods out of operation have a negative effect on the workflow of a laboratory. As various types of samples and other liquids are transferred through tubes, valves and nozzles, there may appear clots which prevent the normal operation of the system.

An automated system for effective screening must provide accurate and reliable measurement results for each measurement even when the rate of measurements is high and when the types of measurements vary between samples. If known instruments could be modified for measuring more effectively a larger number of different kinds of samples, it could be difficult to maintain the required accuracy and reproducibility of the measurements. This concerns, for example, achieving the required accuracy and reproducibility in dispensing volumes and dispensing positions of reagents.

SUMMARY OF THE INVENTION

The present teachings provide an automated instrumentation for assaying and measuring samples wherein described disadvantages of the prior art are avoided or reduced. The object is therefore to achieve effective instrumentation which is usable, e.g. as a genetic screening platform, and capable of performing different kinds of assaying with possibly different chemistries and different kinds of measurements in a reliable and accurate manner.

The object is achieved by providing an automated instrumentation that is based on a finding that a required effectiveness and versatility is achieved by providing in an instrument at least two processing units where a plurality of sample plates are processed simultaneously, and one or several measurement units providing a capability for the instrument of at least two different measurement modes. Such a basic construction gives a possibility to effectively process and measure different types of assays, possibly with different chemistries. It also gives a possibility to apply further features and units which offer reliability and accuracy of assays and measurements even when large numbers of samples are screened using different processes and intensive schedules. The instrument can be implemented with functional modules which may locate one above another. In this manner the versatility and upgradeability of the instrument is achieved.

The teachings also include an automated instrument for assaying and measuring samples, wherein the samples are located on wells of sample plates, and the instrument comprises a plurality of units for processing or storing sample plates, a manipulator for transferring sample plates between the units, and characterized in that the instrument comprises at least one dispensing unit for dispensing reagents or other assay components to the sample wells, at least two units for simultaneously processing or storing a plurality of sample plates, at least one unit for removing substance from the sample wells, and one or several measurement units, the measurement unit(s) providing a capability for the instrument to optically measure samples in at least two measurement modes, and wherein the instrument is self-contained.

The teachings also include a method for assaying and measuring of samples in a self-contained instrument, wherein the samples are located on wells of sample plates, and the method comprises phases in which a sample plate is processed in processing units and the sample plate is moved between the units for processing or storing, characterized in that the method comprises phases in which reagents or other assay components are dispensed to the sample wells, a plurality of sample plates are simultaneously processed or stored in at least two units, substance is removed from the sample wells, and samples are optically measured in at least two measurement modes.

In particular, the samples handled by the instrument and in the method may be sample discs impregnated with blood and located on wells of sample plates.

According to one embodiment, the manipulator has the capability to move the sample plates in three orthogonal directions or combinations thereof and to rotate the sample plates in relation to a vertical axis for transferring the sample plates to the units. That is, the apparatus may have the capability to transfer plates not only to processing/storage units located in one plane but to units located in a very space-saving way within the device. This is of particular importance in the case of sample discs impregnated with blood because their analysis necessarily requires several stages of processing and thus several functional units of the device.

According to one embodiment each unit for processing or storing sample plates has one or several determined locations for the sample plate for the processing or storing, and the units are thus located in the instrument such that the instrument comprises a first unit and a second unit, wherein the projections of the first unit and the second unit on a horizontal plane overlap, the instrument comprises a third unit and a fourth unit, wherein the projections of the third unit and the fourth unit on the horizontal plane overlap, and the determined locations of sample plates at the first unit and the second unit are such that their projections on the horizontal plane do not overlap with projections on the horizontal plane of the determined locations of the sample plates at the third unit and the fourth unit.

According to another embodiment in units for processing or storing sample plates are thus located in the instrument that the instrument further comprises a fifth unit and a sixth unit, wherein the projections of the fifth unit and the sixth unit on a horizontal plane overlap, and the determined locations of sample plates at the fifth unit and the sixth unit are such that their projections on the horizontal plane do not overlap with projections of the determined locations of the sample plates at the first unit, second unit, third unit and the fourth unit.

According to an embodiment the instrument comprises a manipulator for transferring sample plates between interfaces of the units, wherein the manipulator has a capability to move the sample plates in at least two non-parallel directions. The manipulator may have a capability to move the sample plates in up to three orthogonal directions and/or combinations thereof. The manipulator may also have a capability to rotate a sample plate in relation to a vertical axis.

According to an embodiment the instrument comprises at least one plate holder for receiving and holding a sample plate, wherein the plate holder comprises a mechanical interface for the manipulator and for the attachment to inside a processing unit or a storage unit.

In one embodiment the instrument comprises at least two dispenser units for dispensing reagents or other assay components to the sample wells. The instrument may comprise at least three dispenser units for dispensing reagents or other assay components to the sample wells.

According to one embodiment the instrument comprises a first dispensing unit for dispensing substance volumes within a first volume range and a second dispensing unit for dispensing substance volumes within a second volume range, wherein a minimum volume of the first volume range is smaller than a minimum volume of the second volume range, and a maximum volume of the first volume range is smaller than a maximum volume of the second volume range. The two dispenser units may be comprised within a same dispensing module.

According to an embodiment a dispenser unit is arranged to dispense reagent to the sample wells of a sample plate without returning the surplus reagent to the reagent container. A dispensing unit surplus reagent may be arranged to be emptied from the tip into a waste container.

In one embodiment a dispensing unit comprises means for controlling the flow of the reagent in such a way to reduce the amount of reagent flow below a determined threshold flow value during the dispensing. The threshold flow value may be based on an amount of flow needed to avoid the reagent to spread onto the outer surface of the tip. According to an embodiment a dispensing unit is arranged to aspirate each necessary amount of reagent to a sample well without dilution of the reagent in a separate vessel within the instrument.

According to an embodiment the instrument comprises a bulk reagent unit, which comprises at least two reagent containers, at least one pump, and a valve for selectively connecting the pump to a reagent container for transferring reagent from said reagent container to a well of a sample plate and for controlling the amount of reagent to be dispensed to the well of a sample plate.

According to an embodiment the bulk reagent unit comprises a first container for a substance to be dispensed and a second container for the same substance to be dispensed, wherein a dispenser is arranged to dispense the substance selectively from either the first container or the second container, the dispenser is arranged to provide dispensing the substance from the first container and to allow simultaneously changing or filling the second container, and the dispenser is arranged to provide dispensing the substance from a second container and to allow simultaneously changing or filling the first container.

In one embodiment the instrument comprises an arrangement for calibrating the position of a reagent dispensing nozzle in relation to the sample well, wherein the arrangement comprises a test plate comprising a test well, the test well comprises dividing means for dividing the well into at least two sub-wells, the instrument is arranged to dispense liquid to the test well, the instrument is arranged to measure the dispensed liquid from the sub-wells, and the instrument is arranged to repeat the measurement in different relative locations of the nozzle and the test plate and to determine a location for the dispensing where the ratio of the amounts of measured liquid of the sub-wells is closest to a predetermined value. The ratio may be e.g. 1:1.

The test plate may comprise at least two test wells, wherein the means for dividing the first well has a first direction and the means for dividing the second well has a second direction which is perpendicular to the first direction, whereby the instrument is arranged to calibrate the dispensing position in the first direction by means of the second test well, and to calibrate the dispensing position in the second direction by means of the first test well.

According to one embodiment at least two units for simultaneously processing or storing a plurality of sample plates comprise at least two incubator units. The instrument may comprise at least three incubator units.

According to an embodiment least one incubator unit is a shaking incubator. The instrument may comprise at least two shaking incubator units.

In one embodiment the instrument comprises a first incubator and a second incubator, whereby the first incubator is arranged to provide processing in a first processing mode, and whereby the second incubator is simultaneously arranged to provide processing in a second processing mode, which is different from the first mode. In one embodiment the first processing mode is an interval shaking mode wherein shaking is provided in at least two separate time periods and the sample plate is kept inside the first incubator between the at least two time periods, and the second processing mode is a continuous shaking mode wherein shaking is provided for only one time period for a sample plate between loading and removing the sample plate into and out of the incubator.

In one embodiment at least one incubator comprises means for controlling a temperature inside the incubator into an adjustable value within a predetermined temperature range. The at least one incubator may comprise heating means and the maximum value of the predetermined temperature range is substantially above the ambient temperature outside the incubator inside the instrument. The inside temperature of a first incubator can be adjustable into a value, which is substantially different from the inner temperature of a second incubator, thus allowing simultaneous incubation of sample plates in two different temperatures in first and second processing modes.

According to an embodiment at least one incubator comprises an enclosure which can be closed to reduce exchange of air between the inside and outside of the incubator and to reduce evaporation of samples. The incubator may comprise an enclosure for an individual sample plate which enclosure can be closed to reduce exchange of air between the individual sample plate and other sample plates and to reduce evaporation of samples. The mechanical interface for transferring the sample plates in and out of the incubator may comprise a door, which is arranged to be opened for transferring a sample plate in or out of the incubator and which door is arranged to be closed when sample plates are not transferred in or out of the incubator.

In one embodiment of the invention at least one unit for removing substance from the sample wells is a washing unit for washing the wells of the sample plates.

In an embodiment the instrument comprises a fluid unit for delivering wash solution for other units of the instrument for processing sample plates, wherein the fluid unit comprises means for controlling the temperature of the wash solution into a temperature value, which is separately adjustable for each sample plate for which the wash solution is used for. A fluid may comprise a first container for mixing concentrate with water to provide wash solution, and a second container for delivering the wash solution for washing one or several sample plates, and means for transferring a determined amount of wash solution from the first container into the second container for the delivering. The instrument may be arranged to provide mixing in the first container simultaneously with delivering wash solution from the second container for washing of the sample plates.

According to an embodiment the fluid unit comprises means for controlling the temperature of the wash solution of the first container. The fluid unit may comprise means for controlling the temperature of the wash solution of the second container. The fluid unit may comprise a concentrate container for supplying concentrate to the first container. The fluid unit may comprise a connection for an external water inlet in order to supply water for the wash solution. The fluid unit may also comprise a connection for a continuous external waste outlet in order to drain wastes removed from the sample wells or other waste received from the processing units.

According to one embodiment the instrument comprises at least two units for removing substance from the sample wells. At least one said unit for removing substance from the sample wells may be disc remover unit for removing a sample disc from a sample well. The disc remover unit may comprise means for providing an underpressure for guiding substance from the well via an underpressured path, and means for measuring pressure within the path for detecting, whether substance is being removed from the sample well. The instruments may also be arranged to give an error indication if removal of a substance from a sample well is not detected in the disc removing process of the sample well.

In one embodiment the measurement unit is arranged to measure the absorbance of a sample and the instrument is arranged to determine, based on the absorption measurement result, whether the sample disc is in the sample well. The instrument may be arranged to give an indication if a disc is not detected in the absorbance measurement.

According to one embodiment the disc remover unit comprises means for providing an underpressure, i.e. below the pressure of the ambient atmosphere, in an underpressure container, a duct for guiding a sample disc from the sample well to the underpressure container, and means for controlled pressing of the duct by closing and releasing the duct, wherein the means for pressing are arranged to be released for transferring the disc via the duct into the underpressure container, and to be closed for a period between the removal of discs from sample wells of a sample plate. The disc remover unit may have a standby mode, and in the standby mode the open end or a nozzle of the duct is arranged to be set against a counterpart thus preventing an air flow through the duct, and the means for controlled pressing of the duct are arranged to be in a released state.

According to one embodiment the instrument comprises a measurement unit providing a capability to measure samples in at least two measurement modes within said same measurement unit. The measurement modes may comprise time resolved fluorometry (TRF) measurement, prompt photoluminescence (FI) measurement and/or absorbance (ABS) measurement.

In one embodiment the measurement unit is capable of measuring samples in at least three measurement modes, which preferably comprise time-resolved fluorometry (TRF) measurement, prompt photoluminescence (FI) measurement and absorbance (ABS) measurement. The measurement modes may further comprise at least one of following measurement modes:

luminescence measurement,
chemiluminescence measurement.
fluorescence polarization measurement,
Alphascreen measurement, and
radioactivity measurement.

According to an embodiment the measurement unit has a plurality of optical modules, wherein one of the optical modules is selected to be positioned within the optical path of an optical measurement, and wherein the optical module comprises at least one mirror, such as a non-transmitting one, beam splitter or dichroic mirror, and at least one optical filter.

One of the at least one optical filter may be arranged to filter an excitation beam. In one embodiment all optical filters within the path of the excitation beam may be located in the optical module.

One of the at least one optical filter may be arranged to filter an emission beam. In one embodiment all optical filters within the path of the emission beam may be located in the optical module.

One of the at least one optical filter may be arranged to filter an excitation reference beam. The optical filter is e.g. a neutral density filter.

According to one embodiment at least one optical module comprises a lens within an optical path of a measurement.

According to an embodiment the measurement unit comprises a photomultiplier tube for detecting emission, a plurality of optical modules, a measurement mode for time-resolved fluorometry, a measurement mode for prompt photoluminescence, an arrangement for analogue emission signal acquisition, and an arrangement for pulse counting emission signal acquisition, wherein the instrument is arranged to select a first optical module and analogue signal acquisition for performing prompt photoluminescence measurement, and the instrument is arranged to select a second optical module and pulse counting signal acquisition for performing time-resolved fluorometry. The first optical module and the second optical module may have different optical components.

In the time-resolved fluorometry measurement the measurement unit may be arranged to increase the measurement dynamics by controlling the excitation light intensity, optical attenuation of the emission signal or the acquisition delay of the measurement of the emission signal on the basis of activity of the sample being measured. The instrument may further be arranged to define the activity of a sample on the basis of an initial emission measurement.

According to one embodiment the instrument comprises a main control unit for providing a main schedule of processing phases for processing samples on sample plates. A unit for processing samples on a sample plate may comprise a control subunit for controlling the processing function of the processing unit. The control subunit may comprise an interface for connection to the main control unit.

In an embodiment the control subunit is arranged to define a sub-schedule of processing phases for processing samples on sample plates within the unit. The control subunit may be arranged to define the sub-schedule based on a request received from the main control unit.

According to an embodiment the control subunit is arranged to define a sub-schedule for processing samples on a sample plate on the basis of next free time window of a required length. The control subunit may also be arranged to request for a further sub-schedule from another unit, and to define a sub-schedule for processing samples on a sample plate on the basis of said further sub-schedule. The other unit may be a fluid unit, which is arranged to supply liquid for the processing unit for the processing of samples on a sample plate.

According to one embodiment at least two units for simultaneously processing or storing a plurality of sample plates comprise at least one storage unit, and/or stack for loading and/or unloading sample plates.

According to one embodiment at least one unit for simultaneously processing or storing a plurality of sample plates is a plate storage unit for the storage of sample plates. The plate storage unit may also serve as an incubator.

In an embodiment at least one unit for simultaneously processing or storing a plurality of sample plates is a stacker unit for the loading of sample plates into the instrument and/or unloading sample plates from the instrument.

In an embodiment the functionality of loading and/or unloading of the sample plates is available independently on functional states of processing units of the instrument.

In one embodiment the instrument comprises an air dryer for controlling the humidity of the air within the instrument. The air dryer may comprises means for controlling the humidity of the air into a humidity value that is adjustable within a determined range.

According to one embodiment the at least one unit for processing or storing sample plates is a module which is designed to allow installation and removal as a whole to/from the instrument. The module may comprise a front panel with means for positioning to the instrument, wherein the means for positioning are accurately positioned in the front panel in relation to the location for a sample plate in the module, thus allowing a change of a module without individual calibration of the mechanical interface. The means for positioning is e.g. a pin or an aperture.

According to one embodiment,
at least one unit, preferably each unit, for processing or storing sample plates is a module designed to allow installation and removal to/from the instrument,
the apparatus comprises a front panel installed on a stationary position with respect to the manipulator and comprising means, such as a pin or aperture, for positioning the module accurately with respect to the front panel.

Thus, the front panel does not form part of the releasable module but is part of the base of the apparatus. This allows exact positioning of the module with respect to the front panel and thus also with respect to the manipulator.

According to one embodiment, the position of the front panel with respect to the manipulator is adjustable at least in the horizontal plane for allowing exact mutual positioning of the front panel and the manipulator. Typically, the optimal position of each front panel is determined to be in line with trajectories of movement of a pre-assembled manipulator.

According to one embodiment, the front panel at each module place comprises a mechanical interface for a sample plate and the module associated with that front panel can be changed without individual calibration of the mechanical interface and/or re-positioning of the front panel.

According to one embodiment, the front panel(s) is/are designed to significantly contribute to the rigidity of the structure supporting the manipulator. Thus, the weight of the device can be significantly reduced, as the front panels serve both as rigidity-increasing members and as members allowing for fast removal and installation of modules.

In an embodiment all units for processing or storing sample plates in the instrument are modules which are designed to allow installation and removal as a whole to/from the instrument. The instrument may also comprise at least three vertical frames, wherein a module is attached to two adjacent frames. In one embodiment the instrument comprises at least four vertical frames and between each pair of adjacent frames there is at least one module installed.

According to an embodiment the manipulator is located between the four frames, and the manipulator is capable of turning by at least 270 degrees in order to transfer sample plates between all modules installed at the frames. The manipulator and the frames may form an integral unit.

In one embodiment a module can be installed in alternative positions within the frames, whereby the information on the locations of the modules is stored in the system for controlling the movements of the manipulator.

In an embodiment the instrument is capable of assaying samples with at least two chemistries. In an embodiment the instrument is capable of assaying samples with a first chemistry simultaneously with assaying samples with a second chemistry which is different from the first chemistry. According to one embodiment the instrument is adapted to process dried blood spots which are absorbed into a filter paper as samples. According to one embodiment the instrument is adapted to process samples of neonatal screening. According to one embodiment the instrument is adapted to process Delfia assays. According to one embodiment the instrument is adapted to process NCS (Newborn Chemistry System) assays.

According to one embodiment of the method sample plates are processed or stored in units in one or several determined locations for a sample plate, wherein the units and determined locations for sample plates are thus located in the instrument that projections of the first unit and the second unit on a horizontal plane overlap, projections of the third unit and the fourth unit on the horizontal plane overlap, and the determined locations of sample plates at the first unit and the second unit are such that their projections on the horizontal plane do not overlap with projections on the horizontal plane of the determined locations of the sample plates at the third unit and the fourth unit.

In an embodiment of the method the units for processing or storing sample plates are thus located in the instrument such that projections of the fifth unit and the sixth unit on a horizontal plane overlap, and the determined locations of sample plates at the fifth unit and the sixth unit are such that their projections on the horizontal plane do not overlap with projections of the determined locations of the sample plates at the first unit, second unit, third unit and the fourth unit.

In one embodiment of the method sample plates are transferred by a manipulator between interfaces of the processing and/or storage units, wherein the sample plates are moved in at least two non-parallel directions. The sample plates may also be moved by a manipulator in up to three orthogonal directions and/or combinations thereof. A sample plate may further be rotated by a manipulator in relation to a vertical axis.

In an embodiment of the method a sample plate is attached to a plate holder, wherein the plate holder is received to a manipulator and/or to inside of a processing or storing unit at a mechanical interface of the plate holder.

In an embodiment of the method reagents or other assay components are dispensed to the sample wells by at least two dispenser units of the instrument. The reagents or other assay components may be dispensed to the sample wells by at least three alternative dispenser units of the instrument.

In one embodiment of the method substance volumes within a first volume range are dispensed with a first dispensing unit and substance volumes within a substance volumes within a second volume range are dispensed by a second dispenser unit, wherein minimum volume of the first volume range is smaller than the minimum volume of the second volume range, and the maximum volume of the first volume range is smaller than the maximum volume of the second volume range. The dispensing by the first dispensing unit and the dispensing by the second dispensing unit may further be implemented at the same position of a sample plate.

In an embodiment of the method surplus reagent is not returned a reagent container. Surplus reagent may be emptied from the tip into a waste container.

According to one embodiment of the method the flow of the reagent is controlled in such a way that the amount of reagent flow below a determined threshold flow value is minimised during the dispensing of the reagent to a sample well. The threshold flow value may be based on the minimal flow needed to avoid the reagent to spread onto the outer surface of the tip.

In one embodiment of the method each necessary amount of reagent is dispensed to a sample well without dilution of the reagent in a separate vessel within the instrument.

According to an embodiment of the method bulk reagent is dispensed to a sample well by pumping the reagent from a selected bulk reagent container and by controlling the flow of the bulk reagent with individual valve for the bulk reagent container.

In one embodiment of the method reagent or other process substance is dispensed from a first container, and a second container is simultaneously changed or filled with reagent or other process substance, wherein said first and second containers are used in the instrument for dispensing the same reagent/other substance.

In one embodiment of the method the position of a reagent dispensing nozzle is calibrated in relation to the sample well, wherein liquid is dispensed to a test well of a test plate, wherein the test well is divided into at least two sub-wells, the amounts of dispensed liquid is measured from the sub-wells, and the measurement is repeated in different relative locations of the nozzle and the test plate and a calibrated location for the dispensing is determined as the position where the ratio of the amounts of measured liquid of the sub-wells is closest to a predetermined value. The ratio is e.g. 1:1.

In an embodiment the location is calibrated by using two test wells, wherein the first well is divided in a first direction and second well is divided in a second direction which is perpendicular to the first direction, whereby the dispensing position is calibrated in the first direction on the basis of the second test well, and the dispensing position in the second direction is calibrated on the basis of the first test well.

According to one embodiment of the method samples are incubated simultaneously in two incubator units. Samples may be incubated simultaneously in at least three incubator units.

In an embodiment of the method at least one sample plate is shaken during incubation. Sample plates may be shaken in at least two shaking incubator units.

In an embodiment of the method interval shaking is provided in a first shaking incubator, and simultaneously, continuous shaking is provided a second shaking incubator.

According to an embodiment of the method interval shaking is provided in a first shaking incubator and in a second incubator, whereby the first incubator provides processing in a first processing mode, and whereby the second incubator simultaneously provides processing in a second processing mode, which is different from the first mode.

In one embodiment the first processing mode is an interval shaking mode wherein shaking is provided in at least two separate time periods and the sample plate is kept inside the first incubator between the at least two time periods, and the second processing mode is a continuous shaking mode wherein shaking is provided for only one time period for a sample plate between loading and removing the sample plate into and out of the incubator.

In an embodiment incubating temperature inside an incubator is controlled into an adjustable value within a predetermined temperature range.

In one embodiment inside temperature of the first incubator is adjusted into a value, which is substantially different from the inner temperature of the second incubator, and allowing simultaneous incubation of sample plates in two different temperatures in the first and second processing modes.

According to one embodiment the incubating temperature inside an incubator is controlled into an adjustable value within a predetermined temperature range. The inside of an incubator may be heated, whereby the maximum value of the predetermined temperature range is substantially above the ambient temperature outside the incubator inside the instrument.

According to an embodiment of the method at least one sample plate is enclosed in an incubator, wherein an enclosure of the incubator is closed during incubation in order to reduce exchange of air between the inside and outside of the incubator and to reduce evaporation of samples. An individual sample plate may be enclosed in an incubator, wherein an enclosure around the sample plate is closed to reduce exchange of air between the individual sample plate and other sample plates and to reduce evaporation of samples.

A door of an incubator unit may be opened for transferring a sample plate in or out of the incubator and the door is closed when sample plates are not transferred in or out of the incubator.

In one embodiment of the method wells of the sample plates are washed in at least one washing unit.

In one embodiment of the method wash solution is delivered from a fluid unit to other units of the instrument for processing sample plates, wherein the temperature of the wash solution is controlled into a temperature value, which is separately adjustable for each sample plate for which the wash solution is used for.

In one embodiment of the method the concentrate is mixed with water in a first container to prepare wash solution, the wash solution is transferred to a second container, and a determined amount of wash solution is supplied from the second container to a processing unit. That wash solution may be prepared in the first container simultaneously with supplying prepared wash solution from the second container to a processing unit.

In one embodiment the temperature of the wash solution in the first container is controlled at a determined value. The temperature of the wash solution in the second container may also be controlled at a determined value.

According to an embodiment of the method wash concentrate is supplied from a concentrate container to the first container for preparing the wash solution. Water may be supplied to the first container via an external water inlet in order to prepare the wash solution. Waste may be delivered from the units of the instrument via a waste tank to an external waste outlet.

In one embodiment of the method substance is removed from the sample wells in at least two processing units. Removing substance from a sample well may comprise removing a blood sample disc from the sample well.

In one embodiment of the method the disc is removed by providing an underpressure for guiding substance from the well via an underpressured path, wherein pressure is measured within the path for detecting, whether substance is being removed from the sample well. An error indication may be given if removal of substance from a sample well is not detected in the disc removing process of the sample well.

According to an embodiment absorbance of a sample is measured and the instrument is arranged to determine, based on the absorption measurement result, whether the sample disc is in the sample well. An error indication may be given if a disc is not detected in the absorbance measurement.

According to one embodiment of the method the process of removing a disc comprises providing an underpressure, i.e. below the pressure of the ambient atmosphere, in an underpressure container, guiding a sample disc from the sample well to the underpressure container via a duct, and controlled pressing of the duct by opening and closing the duct, wherein the pressing is released for transferring the disc into the underpressure container, and the pressing is activated for a period between the removal of discs from sample wells of a sample plate.

In a standby mode of disc removing the open end or a nozzle of the duct may be set against a counterpart thus preventing an air flow through the duct, whereby the pressing of the duct is in a released state.

According to one embodiment samples can be measured in at least two measurement modes within a same measurement unit. The measurement modes may e.g. comprise time-resolved fluorometry (TRF) measurement, prompt photoluminescence (FI) measurement and/or absorbance (ABS) measurement.

In an embodiment of the method samples can be measured in at least three measurement modes, which can comprise time-resolved fluorometry (TRF) measurement, prompt photoluminescence (FI) measurement and absorbance (ABS) measurement. The measurement modes may optionally or further comprise, for example, at least one of following measurement modes:

luminescence measurement,
chemiluminescence measurement.
fluorescence polarization measurement,
Alphascreen measurement, and
radioactivity measurement.

According to one embodiment of the method the measurement comprises selecting an optical module from a plurality of optical modules, wherein one of the selected optical module positioned within the optical path of an optical measurement, and wherein a light beam is directed within the optical module by at least one mirror, such as non-transmitting, beam splitter or dichroic mirror, and the light beam is filtered within the optical module by at least one optical filter.

In one embodiment the excitation beam may be filtered by said at least one optical filter. The excitation beam may possibly be filtered only within the optical module.

In one embodiment an emission beam is filtered by the at least one optical filter. The emission beam may possibly be filtered only in the optical module.

In one embodiment the excitation reference beam is filtered by at least one optical filter. The excitation reference beam may be filtered by a neutral density filter.

According to an embodiment of the method a light beam is focused or collimated with a lens within the at least one optical module.

According to one embodiment of the method the samples are measured with a measurement mode for time-resolved fluorometry or with a measurement mode for prompt photoluminescence, the emission and/or excitation beam is guided via a selectable optical module, emission is detected with a photomultiplier tube, a photomultiplier tube for detecting emission, and the detected emission signal acquisition is made alternatively with analogue signal acquisition or pulse counting signal acquisition, wherein the first optical module and analogue signal acquisition are selected for performing prompt photoluminescence measurement, and the a second optical module and pulse counting signal acquisition are selected for performing time-resolved fluorometry.

In one embodiment of the method a different processing is made for a light beam in the first optical module compared to the processing in the second optical module.

In time-resolved fluorometry measurement of one embodiment the measurement dynamics may be increased by controlling the excitation light intensity, optical attenuation of the emission signal or the acquisition delay of the measurement of the emission signal on the basis of activity of the sample being measured. The activity of a sample may be defined on the basis of an initial emission measurement.

In one embodiment of the method a main schedule is provided by a main control unit of processing phases for processing samples on sample plates.

In an embodiment of the method processing functions of a processing unit are controlled in a control subunit of the processing unit. Control information may be transferred between the control subunit and the main control unit.

In an embodiment of the method a sub-schedule is defined in the control subunit of processing phases for processing samples on sample plates within the unit. A request may be given by the main control unit to a control subunit and sub-schedule is defined based on a request received from the main control unit.

In one embodiment of the method a sub-schedule for processing samples on a sample plate is defined by the control subunit on the basis of next free time window of a required length for the required processing.

A request may be given by a control subunit for further sub-schedule from another unit, a sub-schedule for processing samples is defined on the basis of said further sub-schedule. The further sub-schedule may be requested from a fluid unit, wherein liquid is supplied by the fluid unit the processing of samples in a processing unit.

In one embodiment of the method sample plates are stored in a plate storage unit of the instrument. Sample plates may possibly also be incubated in the plate storage unit.

In an embodiment of the method sample plates are loaded into the instrument and/or unloaded from the instrument via a stacker unit. Sample plates may possibly be loaded or unloaded simultaneously with processing of other sample plates in any processing unit within the instrument.

In one embodiment of the method humidity of the air within the instrument is controlled with an air dryer. The humidity of the air within the instrument may be controlled into a humidity value that is adjustable within a determined range.

According to one embodiment of the method at least one unit for processing or storing sample plates is installed or removed as a whole module to/from the instrument. A module is positioned to the instrument with positioning means, wherein the positioning means are accurately positioned in a front panel of the module in relation to the location for a sample plate in the module, thus allowing a change of a module without individual calibration of the mechanical interface. The module may be positioned with a pin or an aperture located at the front panel of the module.

In an embodiment of the method all units for processing or storing sample plates in the instrument are modules are designed for installation and removal as a whole to/from the instrument. A module is attached to two adjacent frames of the instrument. Modules may further be installed to each pair of adjacent frames of at least four vertical frames of the instrument.

In one embodiment of the method sample plates are transferred by a manipulator between all processing and storage modules installed at the frames, wherein the manipulator can be turned by at least 270 degrees during the transfer of a sample plate. The manipulator may be attached to the frames.

According to an embodiment of the method a module is installed in one of alternative, available positions within the instrument, whereby the information on the locations of the modules is stored in the system for controlling the movements of the manipulator.

In an embodiment samples are assayed with at least two chemistries. In one embodiment samples are assayed with a first chemistry simultaneously with assaying samples with a second chemistry which is different from the first chemistry. One embodiment of the method is characterized by processing blood spots which are absorbed into a filter paper as samples. One embodiment of the method is characterized by processing samples of neonatal screening. An embodiment of the method is characterized by processing Delfia assays. An embodiment of the method is characterized by processing NCS (Newborn Chemistry System) assays.

The present teachings offer several advantages when compared to prior art instrumentation. These advantages are important, for example, in screening applications, such as neonatal screening, wherein large numbers of samples are processed with various technologies, and wherein the good reliability, accuracy and reproducibility of measurements are required.

The instrumentation allows the alternative measurement modes of the optical measurement, allows alternative assaying sequences, and different assaying sequences can be processed substantially simultaneously. Thus it is possible to process different kinds of assays with a same instrument in an effective manner. For example, it is possible to process both Delfia and NCS assays substantially simultaneously with the instrument.

The instrumentation also allows processing of several phases simultaneously in the instrument. The instrumentation also allows providing same processing phase simultaneously for a plurality of sample plates, and providing a different processing phase simultaneously for a plurality of sample plates. Thus it is possible to efficiently process sample plates of same or different assays.

The instrumentation can be designed to need little floor space since the processing and storing modules can be installed one above another. The modules can also be installed in selected locations. High processing efficiency is achieved because the distances between the modules can be made short, and the required time for transferring the sample plates is therefore small. When a module can be installed, removed and replaced as a whole functional unit, it is easy to make changes and updates in the construction of the instrument.

The instrumentation further allows loading and unloading of sample plates independently of simultaneous processing of other sample plates. Therefore it is possible to load or unload sample plates when the instrument is active. The instrumentation further allows filling or changing dispensing containers independently of simultaneous dispensing. Therefore it is possible to fill or change dispensing containers continuously when the instrument is active. The continuous loading/unloading of sample plates and the continuous filling/changing of dispensing containers increase the efficiency of the instrument. This is because it is not necessary to stop other functions of the instrument during the period of loading/unloading sample plates or filling/changing dispensing containers. It is also not necessary for the user to wait for a moment which is suitable for the processes of the instrument for those procedures. Instead, the user may perform those procedures according to the user's own schedule.

The instrumentation also allows achieving high accuracy and quality of measurements and operation. According to related embodiments high accuracy of dispensing volumes and dispensing position are achieved in dispensing reagents to sample wells. Due to the accuracy it is also possible to dispense small volumes. This allows dispensing without any dilution phase of reagents in separate dilution vessels within the instrument.

According to one embodiment, it is possible to have incubation in e.g. two different temperatures simultaneously for different sample plates of different assays and possibly different chemistries. Further, it is possible to adjust the temperature of the wash solution selectively for each sample plate and each type of assays. These features make it possible to individual temperatures which are specified as optimal for each type of assays. In addition to temperature, it is also possible to control the humidity inside the instrument.

In this patent application term "unit" means an entity for providing a certain function in the instrument. The unit may also have one or several subunits. A unit for processing sample plates may have locations for sample plates for same kind of processing of several sample plates substantially simultaneously. However, if different kind of processing is applied simultaneously for different sample plates, the sample plates are commonly regarded as being processed by different functional units.

In this patent application term "module" means a unit, part of a unit or a combination of units, which is designed for installation and removal as a substantially one block. Modules for different functions may have similar mechanical and electrical interfaces.

In this patent application term "processing a sample plate" may mean any action on the sample plate or the sample or well of the sample plate which may be necessary in the measurement process. The processing may thus include e.g. dispensing, incubating, shaking, washing, optically measuring or transferring a sample plate.

In this patent application "reagent", "process substance" or "process liquid" means substance or liquid which has an active chemical or optical function in the process of measuring the sample.

In this patent application "sample plate" means any substrate for holding a sample to be measured. A sample plate may be e.g. a microtitration plate with 96, 384, 1536 or higher number of wells for samples. Sample wells may be included in the plate or they may be included in removable strips which have a line of sample wells.

In this patent application term "light" means any electromagnetic radiation in optical range and is thus not restricted in any way to the visible part of the light spectrum.

In this patent application term "photoluminescence", "fluorescence" or "excitation" also includes such chemical processes within samples which are activated by applied light.

In this patent application term "measurement mode" means an optical measurement with a specified succession of measurement phases for measuring a property of a sample.

In this patent application term "vertical" means the local direction of the gravitational acceleration on the earth. "Horizontal" means a direction or plane which is orthogonal to vertical direction.

In this patent application term "underpressure" means pressure which has a value below the pressure of the ambient atmosphere.

In this patent application terms "simultaneous" processes and "simultaneously" mean that there exists at least one point of time when concerned processes both/all occur or are active.

In this patent application term "surplus reagent" means reagent which is left at the tip after dispensing reagent to required sample wells.

In this patent application term "sample plate" means any substrate or container which may be used for supporting samples. It need not have a general form of a "plate".

In this patent application term "sample well" means any place or space where a single sample may be placed. The "well" can therefore be e.g. a hollow space with an open or closed top, or a place on a smooth substrate.

BRIEF DESCRIPTION OF THE DRAWINGS

The described and other advantages of the teachings will become apparent from the following detailed description and by referring to the drawings where:

FIG. 3a illustrates an exemplary reagent storage module, FIG. 3b illustrates an exemplary reagent storage cassette, FIG. 4a illustrates an exemplary dispensing module, FIG. 4b illustrates an exemplary low volume pipette, FIG. 5b illustrates an exemplary test sample well for calibration of a dispensing nozzle, FIG. 5c illustrates test sample wells of an exemplary test sample plate, FIG. 6 illustrates an exemplary heated incubator module.

DETAILED DESCRIPTION OF DRAWINGS

Figure 1:
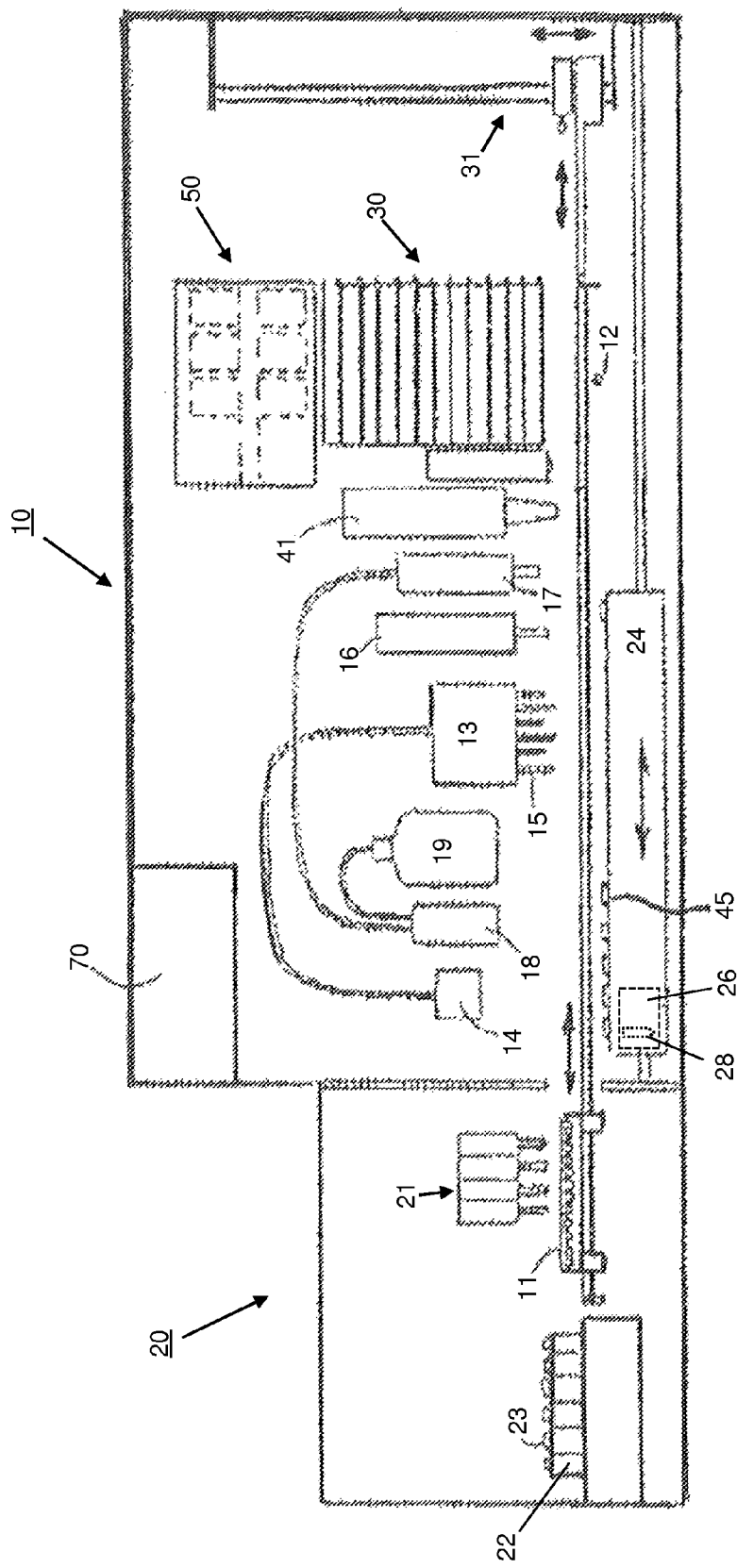
FIG. 1 illustrates an instrumentation, which has automated assaying and measurement of samples.
Figure 2A:
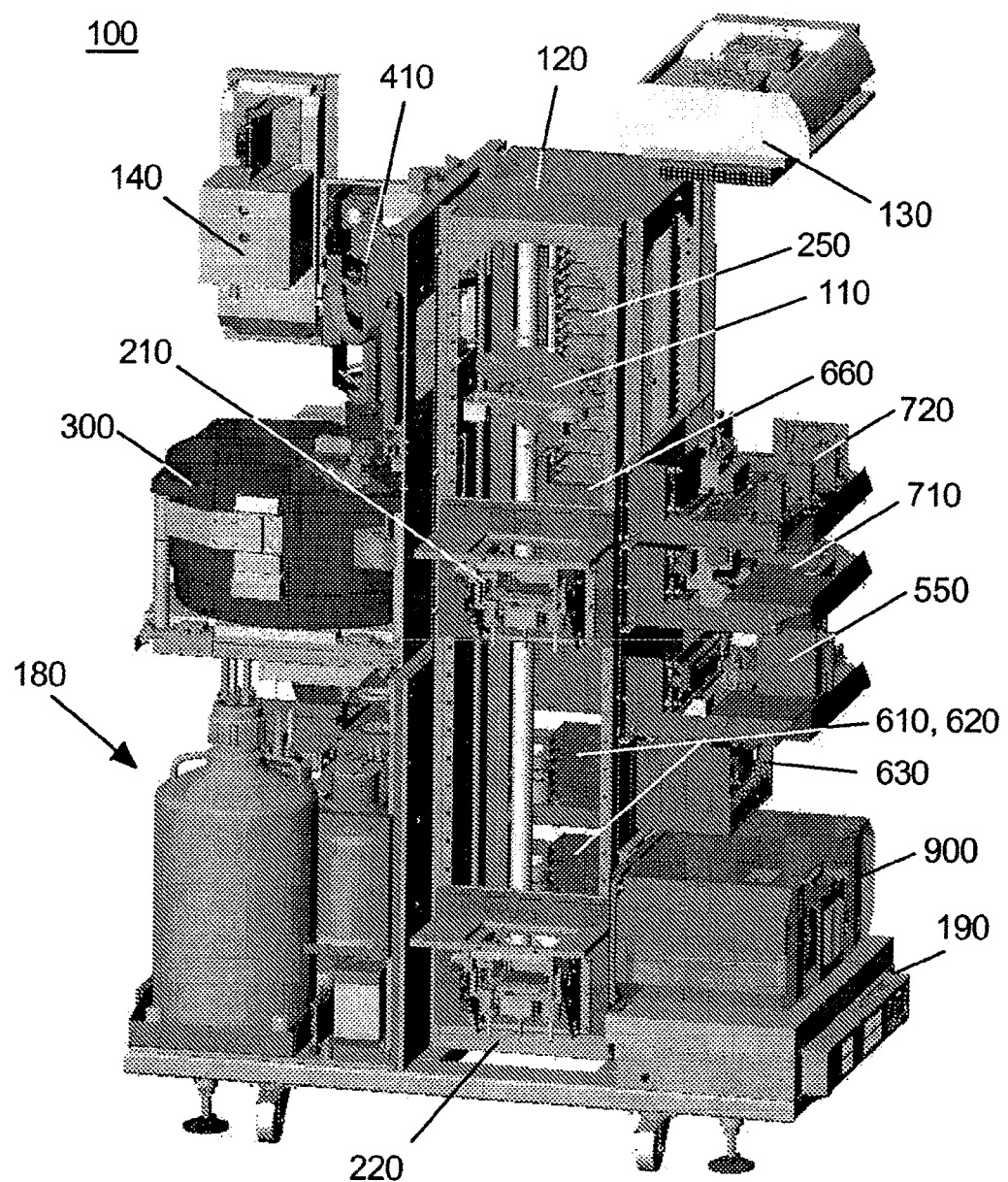
FIG. 2a illustrates an exemplary assembly of instrumentation according to the present teachings.

FIG. 2a illustrates an exemplary automated instrument. The instrument includes following functional units:
- an input stacker unit 210 for loading sample plates;
- an output stacker unit 220 for unloading sample plates;
- a plate storage unit 250 for temporary storing and possibly incubation of sample plates;
- a reagent storage unit 300;
- two dispensing units 410 for dispensing reagents from the reagent storage unit to sample wells;
- a bulk reagent dispenser 550 for dispensing reagents from bulk reagent containers to sample wells;
- a first shaking incubator unit 610, a second shaking incubator 620 unit and a third shaking incubator unit 630 for shaking and/or incubation in fixed temperature;
- an incubator 660 with adjustable temperature and sealed enclosure;

a disc remover 710 for removing blood spot discs from sample wells;

a washing unit 720 for removing liquids from sample wells;

a measurement unit 900 for optical measurement of samples;

a fluid unit 180;

a main control unit and power supply 190;

a manipulator unit 110;

a base frame 120;

a temperature control unit 130; and a dryer unit 140.

Figures 2B, 2C:
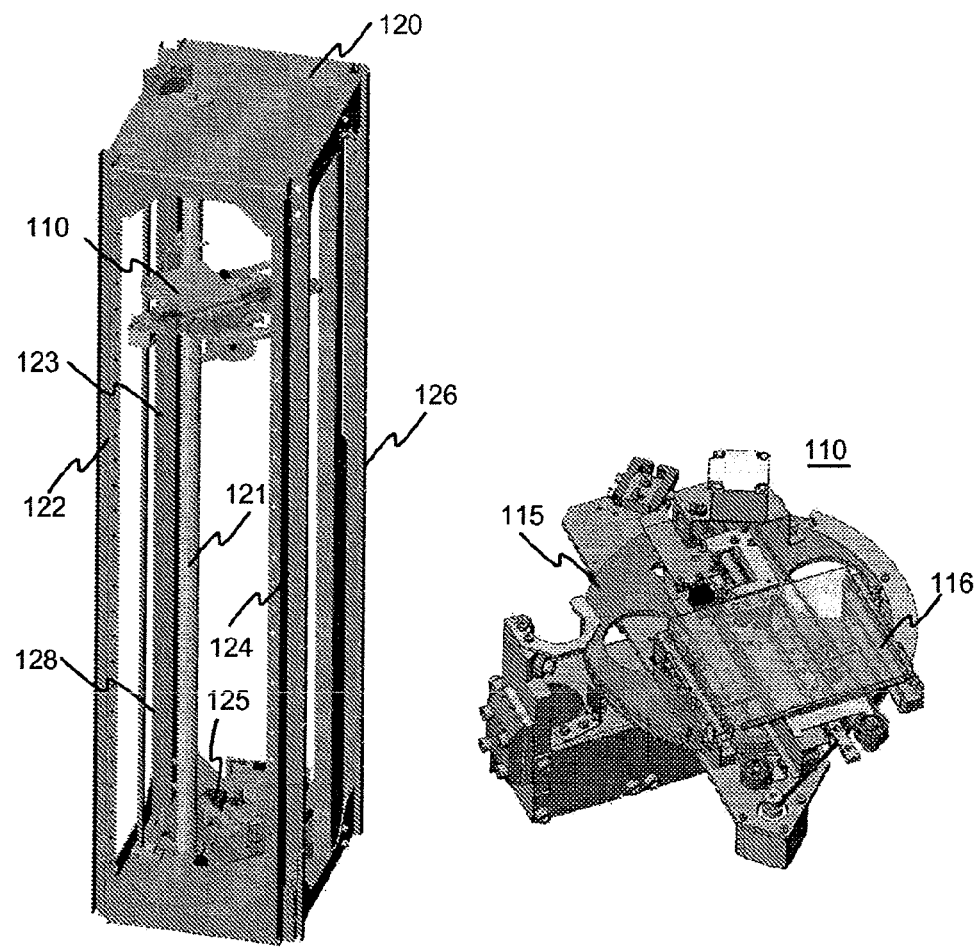
FIG. 2b illustrates an exemplary base frame structure.
FIG. 2c illustrates an exemplary manipulator for transferring sample plates.

The instrument has frame structure 120 as a base which has four vertical frames 122, 124, 126 and 128 as shown in FIG. 2*b*. A manipulator 110 for transferring sample plates is located inside the frame structure and attached to the structure at a separate shaft 121. The base structure also has a step motor 125 which is connected to the manipulator via a toothed belt 123 for moving the manipulator in vertical direction.

The manipulator has a capability to transfer sample plates between the processing and storage modules. Each sample plate is located in a sample plate holder which has a mechanical interface for the manipulator and to each processing/storage unit of the instrument. The manipulator has a carrier 116 which is capable to attach to a sample plate holder. The carrier is coupled to a support 115 which can be rotated 270 degrees in relation to its vertical middle axis. The carrier is also is movable in one horizontal direction in relation to the carrier. Thus the sample plate on the can be controlled to move into any module which is located at the sides of the base frame.

Processing and storage units of the instrument are attached to the frame structure. The processing and storage units of the instrument are modules which are installed to the frame structure as a whole. The modules can be attached to each side of the frame structure and the modules can be attached one above another. Each processing module is specialised for performing a certain processing phase on a sample plate. The sample plates are located inside a processing module during the processing, and therefore the sample plates can be transferred with the manipulator between certain modules independently on the ongoing processes in other modules.

When modules are installed to the frame structure one above another, in one or several "piles", it is possible to provide the instrument within a small horizontal area. Also, the distances between the modules can be made small which reduces the time required for transferring sample plates from one module to another. The locations of the modules in the frame can further be optimised in order to achieve a minimal time needed for the overall transferring of a sample plate during an assay process.

The modules are attached to the frame structure from their front panels. The front panel is attached to two adjacent vertical frames of the frame structure. The front panel has positioning means, such as a pin or a hole, for positioning the manipulator carrier with the module. Further, the positioning means of the front panel of each module have determined positions in relation to the location of the sample plate within the module. This way it is possible to achieve an accurate, determined position between the manipulator and the location of the module in which sample plate is loaded/unloaded. The position information of the unit within the frame detected with the manipulator and stored in the instrument, after which the manipulator is able to load/unload sample plates to/from the unit without a need for manual calibration of the position of the unit during or after the installation of the unit. Thus it is possible to replace modules, change positions of the modules and add new modules in the instrument easily without manual calibration of the position of the module.

Next individual storage and processing modules of the exemplary instrument are described in more detail.

Plate Storage

The instrument has two stacker modules 210 and 220. The stacker modules can be used both as input stackers and output stackers. The loading and unloading of sample plates is made with a plate magazine (not shown in FIG. 2*a*) which can be put to the stacker unit. The stacker unit moves the sample plates between the magazine and the manipulator. In loading sample plates the input stacker connects the sample plates to a plate holder. In unloading sample plates the output stacker releases the plate holders from the sample plates. The manipulator usually transfers the loaded sample plates first to a storage module. Also the processed sample plates are usually first transferred to the plate storage module, wherefrom the manipulator moves them to the output stacker one at a time.

The magazine is operated from underneath by a lifting unit. In the loading operation the elevator rods of the lifting unit lifts the stack of plates, and the indexers that hold plates can be released with a pinch actuator. After this the stack of plates can be moved downwards as far as the wider part of the lowest plate has passed indexers. Next the indexers are closed again with the pinch actuator and rest of the stack remains in the magazine while the lowest plate has been moved in to the plate holder.

Plate storage module 250 is an internal device which stocks up plate holders and plates. All plate holders are located in the plate storage module when they are not used. The plate storage module comprises a set of shelves, one shelf for each plate holder. The usage of plate storage together with stacker modules enables continuous loading of plates independently of processing phases of the processing units of the instrument.

If necessary, it is also possible to use the plate storage module for incubating sample plates in a fixed temperature of the inside of the instrument.

Dispensing Reagents

The instrument has a reagent storage module and a dispenser module for aspirating reagents from the reagent containers of the reagent storage module and dispensing the reagent to sample wells. FIG. 3*a* illustrates a reagent storage module 330 and FIG. 3*b* illustrates a reagent cassette 333 of the reagent storage module.

The reagent storage module is storage for vials and bottles for reagents. The reagents may include buffers, tracers and antibodies for Delfia assays, reagents for NSC assays and/or reagents for possible other assays/chemistries. The reagent storage module is also storage for pipette tips, possibly of various sizes, and caps for preventing evaporation from vials and bottles. The reagent storage may also include one or several dilution vessels which can be used for diluting the reagents with buffer. The reagent storage module may also have a flush basin 333 for flushing tips.

The storage includes separate cassettes for different kinds of items. FIG. 3*b* illustrates an exemplary reagent cassette 333 for Delfia assay. The cassette has a vial 334 for tracer/antibody, a bottle 335 for buffer, a cap 337 for preventing evaporation, and dilution vessels 336. The cassettes may have bar codes for identifying the types of items in each loaded cassette. It is also possible that reagent bottles have bar codes for identification. Correspondingly, the instrument has a bar code reader (not shown in the Figure).

The inside of the reagent storage module is preferably cooled to a temperature below the ambient temperature of the module. The temperature may be controlled to be e.g. +10° C. For this purpose the module has a cooling element, such as a Peltier element, temperature sensor and a control circuit. Due to the low inside temperature the module also has temperature isolating material 338 at its sides and a discharge for possible condensing water. The reagent storage module also has a roof, which is not shown in the FIG. 3a.

The cassettes inside the reagent storage module can be rotated by a controlled motor in relation to the center vertical axis. This way the selected item in the reagent storage can be positioned into the location of usage. It is also possible to use two reagent cassettes for each reagent. This way a cassette with empty bottle can be changed and/or filled without interrupting the process of the instrument. The reagent storage has an opening 331 with a movable lid for loading cassettes. When a bottle in a cassette become empty a controller of the instrument may rotate the set of cassettes so that the cassette to be filled is positioned at the opening for loading.

FIG. 4a illustrates an exemplary dispenser module 440 which includes two dispenser units. A small volume dispenser 444 may dispense e.g. volumes within range 5-50 pl, and a large volume dispenser 448 may dispense e.g. volumes within range 50-200 pl. The aspiration and dispensing is based e.g. on pumping a system liquid in a pipette for providing an effect of aspirating reagent into a pipette or dispensing reagent into a sample well, for example.

The dispenser module has a conveyor 441 which holds the sample plate at a controlled position 480 during the dispensing. The conveyor can be moved with controlled motors in two horizontal, orthogonal directions. This way each sample to be dispensed is moved to the location of dispensing under a dispensing pipette. The dispensing pipette 444, 448 is moved in vertical direction during the dispensing. However, the pipette is also required to move in a horizontal direction between the positions of aspirating and dispensing, for example. The dispensing module has mover mechanisms 442 for moving the pipettes.

The dispensing unit has functionalities for aspirating reagents and buffers from vials and bottles, diluting reagents in a dilution vessel, dispensing reagents to sample wells, and handling evaporation caps of the vials/bottles. The dispensing module also monitors the liquid levels of the reagents in the vials and bottles, and detects presence of evaporation caps and dispensing tips in the reagent storage module.

FIG. 4b illustrates a low volume pipette which may dispense e.g. volumes of range 5-50 pl. The figure shows a pipette tip 447, a motor driven piston 445 and a pressure sensor 446. Dispensing small volumes requires high absolute accuracy in dispensing in order to achieve a required relative accuracy of the dispensed volumes. For example, the requirement for the relative reproducibility may be as small as 1.5%. However, the ability of dispensing such small volumes accurately often means that it is not necessary to dilute a reagent. This decreases the overall time required for dispensing and thus increases the efficiency of the whole process.

The required accuracy of dispensing is achieved by steps described in the following. The tip of a pipette may first be first coated with reagent by filling and emptying the tip with reagent for a few times. During this procedure the inner surface of the tip will be coated with a thin layer of reagent. When the layer of reagent is formed before dispensing reagent to the sample wells, the forming of such a reagent layer does not affect the reproducibility of dispensing volumes.

After coating a suitable amount of reagent is aspirated into the pipette tip for dispensing. During the coating and aspirating pressure at the input hose of the dispenser is simultaneously measured with a pressure sensor. With pressure measurement it is possible to detect several kinds of phenomenon which might affect the aspirating negatively:

It is possible to detect when the tip touches the surface of the reagent and it is thus possible to ensure that the end of the pipette tip is well under the surface of the reagent during the whole aspiration;

It is possible to detect surface of the bottle floor, and thus detect if the tip is too near the bottle floor for the aspiration and if there is too small amount of reagent for the aspiration;

It is possible to detect a leakage of the tip;

It is possible to detect if the hole of the tip is not of the right size; and

It is possible to detect possible malfunctioning of the pipette.

In case of detecting an erroneous function, the user may be informed of e.g. the necessity to fill in reagent, or the instrument may e.g. replace a defective tip automatically. It is thus possible to improve the reliability of aspirating by monitoring the pressure at the pipette.

The reagent is dispensed to a sample well slightly above the surface of the sample well. During the dispensing of reagent to the sample wells, a drop of reagent may be formed at the end of the tip and at the outer surface of the tip end. The formation of such a drop would degrade the reproducibility when dispensing small volumes. This problem is solved by a determined control of the reagent flow from the tip. It has been discovered by the inventors that a drop may be formed if the flow of the reagent is below a determined threshold value. This threshold value can be predetermined for each reagent and pipette type which is used. When the flow is above the threshold value drop formation does not take place. Thus the problem can be solved by increasing the flow rapidly above the threshold flow value at the start of the dispensing, and by decreasing the flow rapidly from the threshold flow value to zero at the end of the dispensing. This way it is possible to avoid or decrease a drop formation and achieve goad reproducibility of small volume dispensing.

Figure 4C:
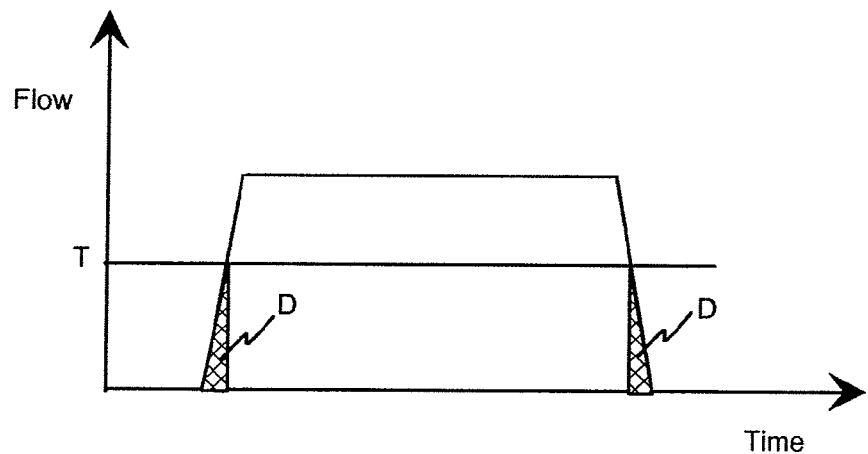
FIG. 4c illustrates an exemplary diagram for accurately controlling reagent flow.

FIG. 4c illustrates a diagram of an exemplary reagent flow as a function of time during dispensing. The predetermined threshold value of flow is denoted as °T". In the present method most of the dispensing is made using flow values which are above the threshold value. A possible drop is formed during the time when the flow value is below the threshold value. The maximum size of the drop is a time integral D of flow for those time periods. It is thus preferable to minimize the integral by increasing and decreasing the value of flow rapidly i.e. to use a high acceleration of flow in the beginning and high deceleration in the end of the dispensing. It is preferable that the integral is smaller than the requirement for accuracy and/or reproducibility of the dispensing. Such requirement may be e.g. 10%, preferably 3% or more preferably 1.5% of the volume to be dispensed. It is also preferable that said integral is smaller that the largest size of a drop which is able to remain at the end of the tip.

In order to achieve a sufficiently high acceleration and deceleration of flow a strong step motor may be used. The step motor thus moves the piston of the pipette with e.g. a threaded transmission. It is preferable to design the transmission ratio to be such that the step motor always turns exactly one or multitude of whole revolution when dispensing a dose. This way it is possible to compensate possible nonlinearities in the transmission mechanics. It is also preferable to use fast control of the step motor.

The pressure of the pipette may be monitored also during the dispensing. By pressure monitoring it is possible to detect if a drop is formed at the tip end. It is also possible to detect if there is foam within the reagent. It is also possible to detect other erroneous functions as e.g. was disclosed above.

It is necessary to aspirate such amounts of reagents to the pipette that some reagent remains in the tip after dispensing the last well of a sample plate. The remaining surplus reagent may be returned to the reagent container or emptied into waste. It may also be necessary to dispense reagent first in the reagent container before the start of dispensing the sample wells. When reagent is dispensed or returned to the reagent container it may be preferable first to immerse the tip of the pipette below the reagent surface before outputting the reagent to the reagent container. This is because the outputting the reagent from above the reagent surface might cause foam formation at the reagent surface. Such foam within the reagent might degrade the accuracy of the dispensing volumes.

The features described above may also be used in a large volume pipette. When an instrument has both a low volume dispenser and a large volume dispenser it is possible to dilute reagents within the sample well without a need for a separate dilution vessel. A required amount of a dilution buffer may be first dispensed to a sample well and a required amount of reagent may be dispensed with the small volume dispenser to the same sample well. Thus a diluted reagent is provided to sample wells by alternately dispensing reagent with a low volume dispenser and buffer with a large volume dispenser. This way it is possible to provide the dispensing in a shorter time period compared to using a separate dilution vessel. It also makes the use of the instrument easier because the user does not need to handle dilution vessels.

Figure 5A:
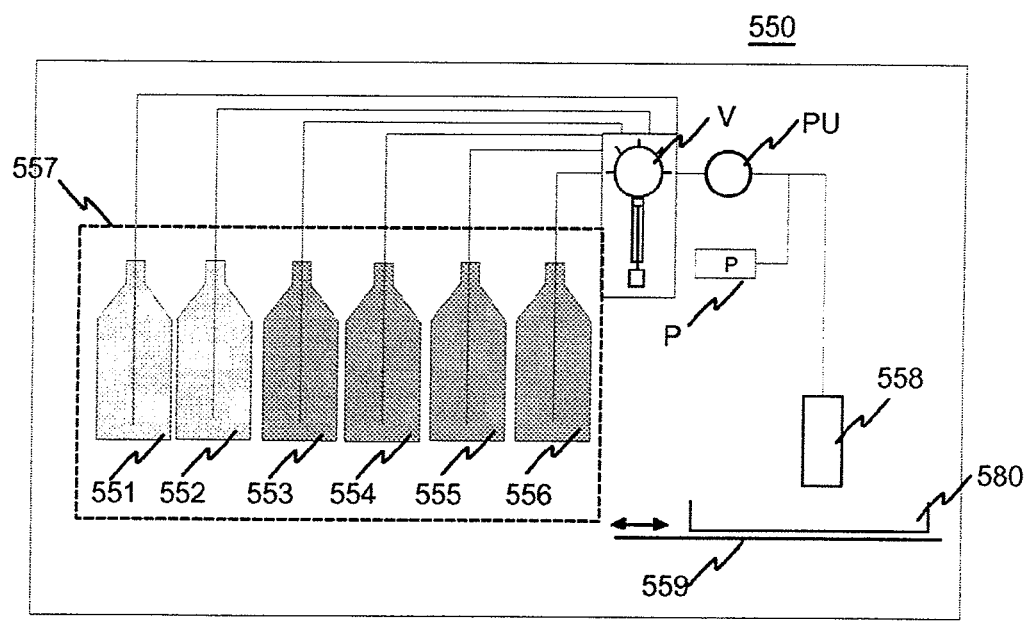
FIG. 5a illustrates a reagent flow diagram of an exemplary bulk reagent dispenser.

FIG. 5a illustrates an exemplary bulk reagent unit 550. The unit consists of a bulk reagent dispensing module for dispensing bulk reagent and a reagent container sub-unit 557. The bulk reagent dispensing module is used to dispense bulk reagents into wells of a sample plate. The module consists of a dispensing head 558, a dispensing pump PU and a conveyor 559 for holding a sample plate and moving it in one horizontal direction. The dispensing head moves along and above the strips of the sample plate. The conveyor moves the plate so that the dispensing head can reach each well. The dispensing pump gives a dosage of liquid in each sample well which is assayed.

The bulk reagent dispensing module comprises dispensing pumps connected to bulk reagent containers, such as bottles. There is one dispensing head in each pump and multi-way valve V that connects the pump PU to reagent bottles 551-556. There may be one pump for dispensing from all bulk reagent bottles or there may be one pump for dispensing each reagent. Pressure or flow of reagent is measured with a sensor P. This way it is possible to detect erroneous functions as was described above in relation to the low volume dispenser.

The bottle support is a separate sub-unit which is located at the door of the instrument. The bottle support may have places for e.g. six or eight bottles, two bottles for each of four different bulk reagents. The bulk reagent unit has e.g. three pumps for dispensing. There may be one pump for each different reagent or one pump may be used for two or several different reagents. There may be sensors installed beside the bulk reagent bottles for detecting the amount of reagent at each bottle. Especially, it is useful to detect whether there is bulk reagent available or whether the bottle is too empty for dispensing.

The bulk reagent container sub-unit has two reagent containers for each bulk reagent. Thus reagent bottles 551 and 552 both contain same reagent, reagent bottles 553 and 554 both contain same reagent and reagent bottles 555 and 556 both contain same reagent. It is thus possible to fill or change an empty bulk reagent bottle during the same reagent is used for dispensing from another reagent container. This allows filling and/or changing the bulk reagent containers continuously, independently of the processing phases of the instrument. Thus the bulk reagent containers can be changed or filled according the user's own schedule instead of the schedule of the instrument.

The bulk reagent unit may also have a bar code reader. It can be used for inputting data concerning the type of bulk reagent when a new bulk reagent bottle is installed. The bar code reader reads the bar code from the bulk reagent bottle. It is also possible to provide light or other indication for each bulk reagent bottle, showing which bottle is required to be filled/changed. The bulk reagent unit may also have a flush basin for flushing tips.

In order to achieve good accuracy and reproducibility in the dispensing volumes it is possible to use the similar procedure in dispensing bulk reagents as was described in relation to the small volume pipette. The flow of dispensed liquid is increased rapidly with high acceleration above threshold flow value at the start of the dispensing, and at the end of dispensing the flow is decreased rapidly with high deceleration from the threshold flow value to zero at the end of the dispensing. This way it is possible to avoid or decrease a drop formation and achieve good accuracy and reproducibility of volumes in dispensing. It is preferable that the dispensed volume during flow below the threshold value is smaller than the requirement for accuracy and/or reproducibility of the dispensing. Such requirement may be e.g. 10%, preferably 3% or more preferably 1.5% of the volume to be dispensed.

It is preferable to dispense the liquid against a vertical wall of a sample well in order to avoid or decrease formation of foam. This is achieved by positioning the dispensing nozzle oblique in relation to vertical direction. The relative positions of the dispensing nozzle of the bulk reagent unit and a sample plate need to be accurate in order to have the reagent volumes dispensed totally into correct sample wells. FIGS. 5b and 5c illustrate an exemplary test plate which can be used instead of a sample plate for calibrating the relative positions of the sample plate and the nozzle.

The test plate has at least one test well 571, which is divided by a partition 574 into at least two sub-wells 572 and 573. The bulk dispenser is then controlled to dispense liquid 576 from a nozzle 575 to the well. The partition is located in the sample well in such a way that e.g. approximately same amounts of liquid is dispensed to the both sub-wells when the relative positions of the nozzle and the sample plate are correct. The instrument is then controlled to measure the dispensed liquid from the sub-wells. The measurement can be made with a dispenser unit by measuring the height of the liquid surfaces at both sub-wells. For example, a large volume dispenser may be used for this measurement.

The instrument is arranged to repeat the measurement in different relative locations of the nozzle and the test plate and to determine a location for the dispensing where the ratio of the amounts of measured liquid is closest to a predetermined value. This predetermined value of the ratio may be e.g. 1:1, so that the amounts of liquid in both wells are is same when the relative positions are correct. Between the repeated measurements the test well may be emptied in a module for removing substance from sample plates, such as the disc remover module. The number of required measurements can decreased by using iteration in selecting the successive positions of the test plate in the calibration process.

FIG. 5c shows a test plate with two test wells for calibrating the relative position in two orthogonal directions. Then, a partition 574*a* of the first test well 571 *a* has a first direction and the partition 574*b* of the second well 571*b* has a second direction which is perpendicular to the first direction. The instrument is then arranged to calibrate the dispensing position in the first direction by means of the second test well, and to calibrate the dispensing position in the second direction by means of the first test well in a manner described above.

Incubating

The exemplary instrument of FIG. 2*a* has four incubators. Three of the incubators, 610, 620 and 630 have a capability of shaking the sample plates during the incubation, and the incubation is performed in the fixed inner temperature of the instrument. The incubation temperature may be e.g. 25° C. The fourth incubator module 660 is a non-shaking incubator module wherein the incubating temperature can be controlled into an adjusted value within a determined temperature range. It is also possible to use the plate storage module for non-shaking incubation in the fixed inner temperature of the instrument.

The shaking incubator module provides an incubation area for sample plates, which require shaking incubation to accelerate chemistry reaction in the wells of a sample plate. The plates inside the incubator are on individual shelves, which are vertically stacked on each other. The shaking incubator has shelves for six sample plates. The shelf moves in a circular-formed path and thus shakes the sample plates. The diameter of the path may be e.g. 2 mm. The movement is achieved with a dc motor which is connected to the plate rack with a belt and eccentric axles. There are counter weights in the axle for balancing the movement. An exemplary shaking incubator is described in the patent document U.S. Pat. No. 5,346,303.

All incubators have a plurality of locations for sample plates, and it is thus possible to incubate a plurality of sample plates simultaneously in each incubator module. When the instrument has at least two shaking incubator modules it is possible to provide two different types of shaking simultaneously. A first shaking incubator may be controlled to provide continuous shaking and a second shaking incubator may be controlled to provide interval shaking If different sample plates require different type of shaking the two shaking incubator modules allow the possibility to incubate such sample plates simultaneously without a need for queuing.

FIG. 6 illustrates an exemplary heated incubator module 660. The heated incubator provides a heat insulated non-shaking area for sample plates, which need elevated incubation temperature. The inside of the incubator module can be electrically heated with e.g. a heating resistor element 664 into an adjusted temperature above the main temperature inside the instrument. The adjustment range may be e.g. 25° C.-37° C. The heating is controlled on the basis of the temperature adjustment and a signal received from a temperature sensor (not shown in FIG. 6) within the incubator.

The heated incubator unit has individual sealed enclosures 620 for sample plates to reduce evaporation of samples. The exemplary incubator has enclosures for 12 sample plates. The enclosures inside the incubator are vertically stacked above each other. The heated incubator module has a sliding door 661, which is temperature isolated like the walls of the incubator. The door is at the entrance of the sample plates, and the door is opened and closed by a controlled step motor 662. The door is opened when a sample plate is transferred in or out of the incubator, and the door is controlled to a closed position when sample plates are not transferred to/from the incubator in order to reduce exchange of air between the inside and outside of the incubator and to reduce evaporation of samples.

FIG. 6 also shows the front panel 665 for attaching the module to the frame structure of the instrument.

It may be useful to shake the sample plates in a shaker before applying the sample plates into the heating incubator. A short shaking mixes the liquids and reagents in the wells and thus starts the desired reaction.

When the instrument has at least two incubator modules wherein at least one incubator module has an adjustable temperature it is possible to provide simultaneously incubation for two types of assays/chemistries which require different incubation temperatures.

Substance Removal

One of the units for removing substance from sample wells is a disc remover module. In this module sample discs and liquid are removed from the sample plate. Sample disc is a punched piece of a filter paper wherein a blood spot is absorbed. The disc remover may also be used for emptying the sample well from liquid for interrupting a reaction in timed processes. Such an interrupting synchronized in time with dispensing reagents. The disc remover may also empty the sample plate when the assay is finished.

The disc removal process is based on creating underpressure for providing suction. In the disc remover there is one suction head connected to an underpressure tank with a duct. The suction head moves in one horizontal direction above the plate and a conveyer of a sample plate moves in another, perpendicular direction so that the location of each sample well can be reached by the nozzle. Vertical movement allows the head enter into the wells of the plate. During the removal cycle, the duct from the suction head to the tank is opened and due to vacuum the disc and liquid flows into the vacuum waste tank.

Figure 7A:
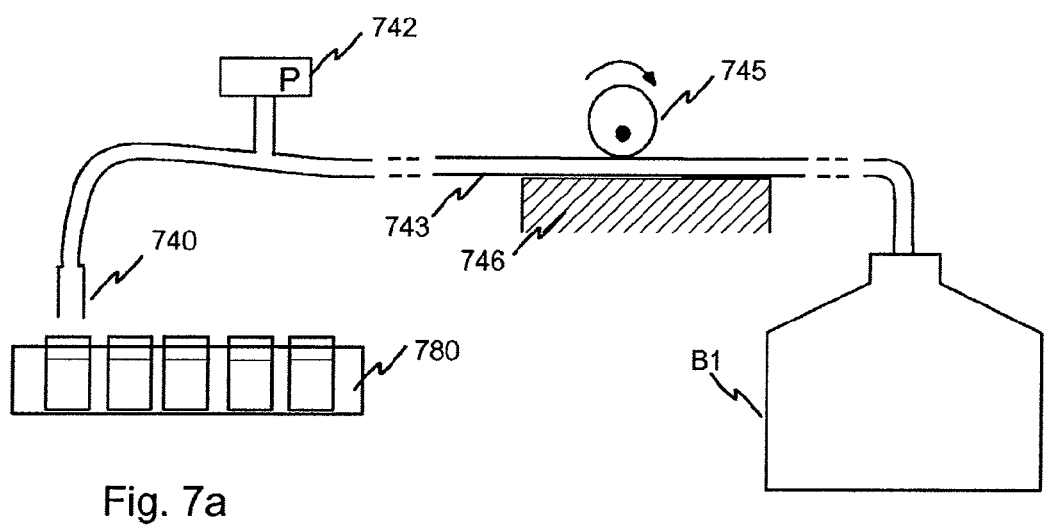
FIG. 7a illustrates substance flow in an exemplary disc remover module of instrumentation when a duct is open for substance flow.
Figure 7B:
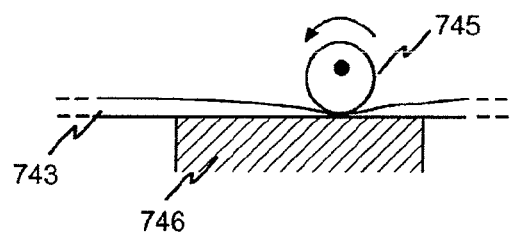
FIG. 7b illustrates an exemplary valve in a pressed state for preventing substance flow.

The control of the suction can be made by controlling a valve installed at the duct. However, the flowing substances easily block the moving parts of a valve which may cause malfunction of the substance removal. This can be solved by using a duct with at least slightly flexible shell. FIGS. 7*a* and 7*b* illustrate such an arrangement. A flexible duct 743 can be closed by pressing the duct and opened by releasing the pressing. Such a controlled clamping/releasing function can be implemented with e.g. an eccentric, which is connected to a controlled step motor.

In FIG. 7*a* there is a wheel 745 and a fixed base 746 at opposite sides of the duct 743. Wheel 745 is eccentric and can be rotated by a step motor. When the wheel 745 is at the shown position the duct is open. The waste tank 131 has an underpressure, which causes suction at the suction head 740, thus removing sample discs from the sample wells of the sample plate 780. When the wheel 745 is rotated by half a cycle the duct becomes pressed as shown in FIG. 7*b*. In this position there is no flow in the duct due to the underpressure.

The disc remover may also have a flushing vessel for flushing the suction head. In a standby state of the disc remover module the suction head can be positioned at against bottom of the flush tank. The duct clamp is released, and the underpressure of the duct presses the suction head against the bottom of the flush tank. Thus the suction head is closed tightly against the bottom of the flushing vessel. It is useful to keep the duct clamp released at the standby state because a continuous clamping of the duct for a long time might damage the duct.

The clamping of the thus duct can be released by positioning the nozzle against a counterpart, such as the bottom of the flushing vessel, during the standby state.

The disc remover may also have a pressure sensor or a flow sensor which monitors the flow at the duct or the nozzle. A pressure sensor 742 is shown in FIG. 7*a* installed between the nozzle and the eccentric valve. The pressure sensor may be used for detecting whether there is liquid inside a sample well or whether the well is empty. It is also possible to detect possible blockages at the suction head or the duct and any other malfunctions which affect the suction and flow of substances from the sample wells.

The exemplary instrument also has another unit for removing substance from sample wells, a wash module. The wash module is a device which washes wells of sample plates. The washer has a manifold which has a capability to wash e.g. 24 sample wells at once. A sample plate moves horizontally on a conveyor of the wash module in one direction, and manifold is set above the plate conveyor and it moves vertically during the wash process. The washing is based on underpressure in the waste tank and on overpressure in the duct led from the wash solution bottle. One valve controls wash solution flow and another valve controls suction. During the washing the wash solution is fed with one nozzle, and the washing solution and possible other liquids are removed from the well with another nozzle. The wash unit may also have a flush vessel for flushing the nozzles.

The wash module may have a flow sensor for monitoring the flow of the wash solution and flush solution, in order to detect any malfunction such as blockages in a duct or a valve.

The wash module washes the wells of a sample plate with wash solution, which has a controlled temperature of e.g. 25° C. The wash module may also remove liquids from the wells before or after the measurement. When the wash is made before the measurement it may be necessary to use wash solution of specified temperature. Therefore the temperature of the wash solution may be adjusted individually for each sample plate within a determined temperature range. The wash solution is received from a fluid unit, and the temperature adjustment of the wash solution is further discussed below.

Fluid Delivery

Figure 8:
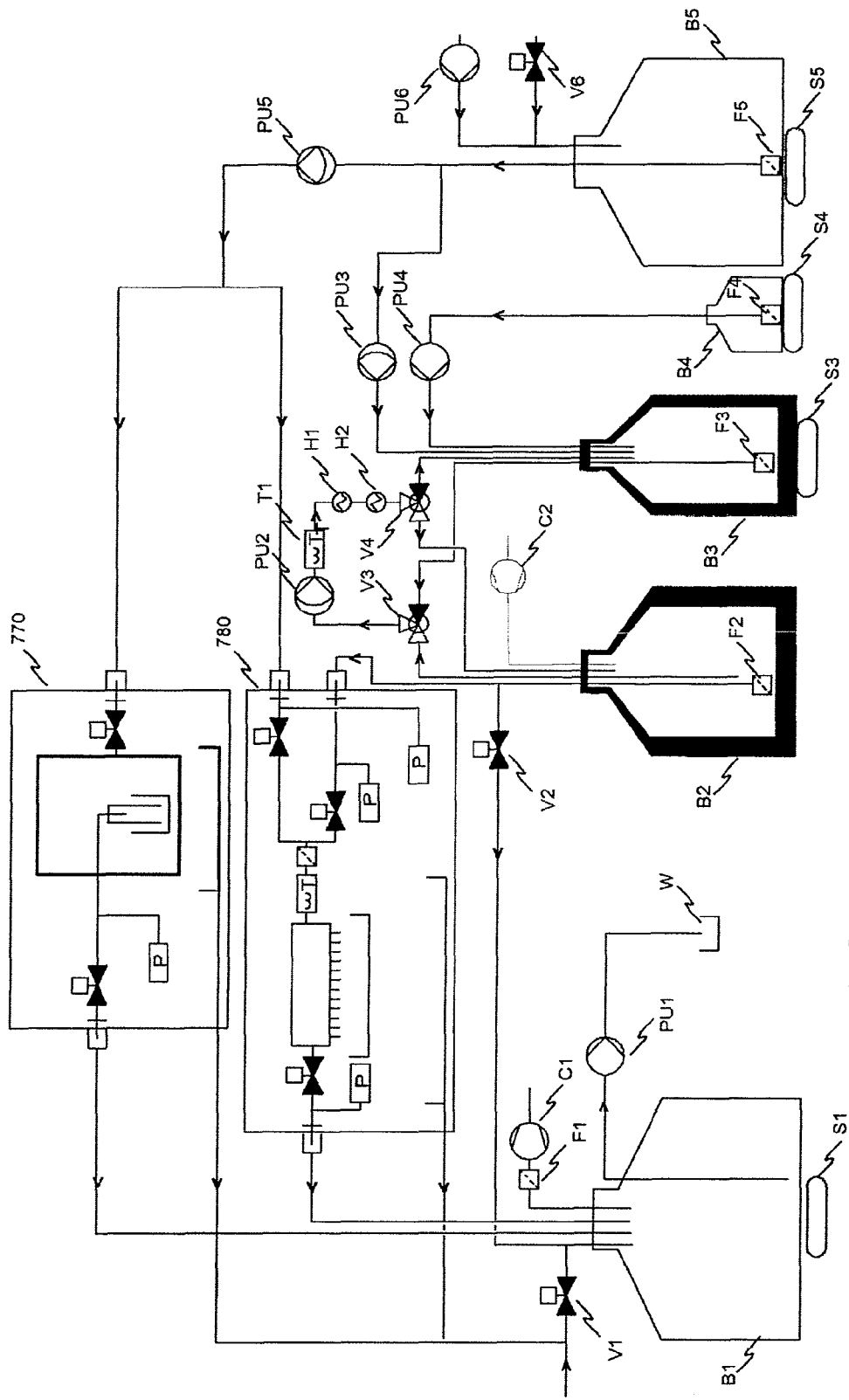
FIG. 8 illustrates an exemplary fluid unit.

The exemplary instrument described above has a fluid unit which provides fluids to processing modules and acquires waste from the processing units. FIG. 8 illustrates main parts of a fluid unit of the exemplary instrument. The fluids required by the processing units include wash solution and flush liquid.

The fluid unit comprises a bottle B5 for purified water. The bottle is filled with water with pump PU6 from an external container, or from a pressurized water inlet via valve V6. The water tank can be filled in two alternative ways. The instrument can be permanently connected to the pure water system of a laboratory. The processor fills the water tank by opening the valve V6 and, based on the internal pressure of the laboratory water system, causing the water to flow from the laboratory system into the tank. Alternatively it is possible that the instrument pumps water into the water tank from an external water container. The amount of water in the bottle B5 can be measured with a scale S5 which carries the weight of the bottle. The weight information can thus be used for automatic filling of the bottle when the amount of water has decreased below a specified value.

The purified water is used for preparing wash solution and as flush liquid in several processing modules for e.g. flushing tips and nozzles. A pump PU5 aspirates flush water from the bottle B5 and creates an overpressure at the flush water duct which is led to processing modules. FIG. 8 shows a disc remover module 770 and a wash module 780 which both have a connection for flush liquid input. Flush liquid may also be used in e.g. dispensing module and bulk reagent module.

The fluid module prepares wash solution by mixing wash concentrate with purified water. A pump PU3 pumps purified water from the bottle B5 into a mixing container B3. Pump PI-14 pumps wash concentrate from a wash concentrate bottle B4 into the mixing bottle B3. The amount of pumped liquids is measured with a scale S3 which is located under the mixing bottle B3 and carries the weight of the bottle. The amounts of pumped water and wash concentrate are determined by the amount of required wash solution and the specified mixing ratio between concentrate and water. A suitable mixing ratio between the concentrate and water may be e.g. 1:25. The bottle B4 for wash concentrate is installed on a scale S4 which gives information on the amount of concentrate in the bottle B4. This information can be used for reminding the user of filling the wash concentrate bottle when the amount of concentrate has decreased below a specified value.

The wash concentrate and water are mixed by circulating the fluids of the mixing bottle B3 with a pump PU2 through valves V3 and V4. The temperature of the wash solution can also be adjusted into a selected temperature value during circulating the wash liquid of bottle B3. The temperature of the wash solution is measured with a temperature sensor T1 located at the circulation tubing. The circulating wash solution is heated with heat exchangers HI and H2 if necessary. The circulation is activated and controlled with a pump PU2 and valves V3 and V4.

After the wash liquid has been mixed and the correct temperature has been achieved, the wash liquid is transferred from the mixing bottle into wash solution bottle B2 via a pump PU2 and valves V3 and V4. The amount of transferred wash solution can be measured and controlled on the basis of the weight information received from the scale S3. It is also possible to transfer wash solution from the wash solution bottle B2 back to the mixing bottle B3 if there is a surplus of wash solution in the wash solution bottle B2. It is also possible to circulate the wash solution of the wash solution bottle B2 through the valves V3 and V4, pump Pu2 and heat exchangers H1 and H2 back to the bottle B2. This way it is possible to regulate the temperature or mix the wash solution of the wash solution bottle B2

A compressor C2 is connected to the wash solution bottle for producing an overpressure inside the bottle. The wash solution is delivered via a duct to the wash module, and due to the overpressure of the wash solution, the wash solution will flow after a related valve is opened in the wash module.

When separate mixing bottle and wash solution bottle is used it is possible to deliver wash solution to the wash module from the wash solution bottle B2, and simultaneously mix wash solution in the mixing bottle B3 for the washing needs of following sample plates. With such a simultaneous delivery and mixing processes it is possible to avoid waiting periods in washing and achieve a good efficiency.

The temperature regulation allows an individual adjustment of wash solution temperature for each sample plate. Thus it is possible to process different types of assays which require different wash temperatures. The temperature regulation of wash solution with e.g. the described circulation process is possible even is a common bottle is provided for both mixing and delivering wash solution.

Wash solution may also be used as a system liquid in a dispensing pipette. The system liquid can be led from the wash solution bottle to the dispensing unit with a separate duct and valve (not shown in FIG. 8). The wash solution bottle may have a separate cup at the bottom of the bottle for supplying system liquid for the dispensing module. Thus the cup will include system liquid even if other wash solution has been used from the wash solution bottle via other output duct(s).

The output ducts of the bottles B2-B5 may have filters F2-F5 for preventing possible particles from entering the processing units.

The exemplary fluid unit also has a waste tank 131 for collecting waste from several modules, such as wash module, disc remover, bulk reagent dispenser, wash solution container and possible collection vessels. Collection vessels can be used e.g. for collecting condensed water and overflow liquids. An underpressure, such as vacuum, is created into the waste tank 131 with a compressor C1, which is connected to the waste tank via a filter F1. The flow of waste to the waste tank 131 can be controlled with a common valve V1 and valves in processing modules, such as the disk remover module 770 and the wash module 780. The underpressure of the waste ducts can be used for the suction of the discs and other liquids from sample wells in the disc remover module 770, and for the suction of wash solution and other liquids from sample wells in the wash module 780.

The amount of waste is measured with a scale S1 which is located under the waste tank 131 and which carries the weight of the tank. When the amount of waste has reached a specified value the waste may be automatically transferred from the waste tank to an external waste outlet W. The waste is transferred to the outlet with a controlled pump PU1. The waste outlet may be e.g. a fixed drain or an external tank.

It is thus possible to provide an automated filling of water directly from an external water supply, and to provide an automated emptying of waste directly to an external drain. Such automated functions decrease the required manual work of the user. With the automated functions it is also possible to prevent breaks in the functionality of the instrument due to belated filling or emptying of the tanks.

Optical Measurement

The instrument according to the invention has a capability to perform optical measurements of samples with at least two measurement modes. It is useful if the instrument has a capability to perform optical measurements of samples with at least three measurement modes. The measurements of different measurement modes may be provided in a single measurement unit or separate measurement units. The exemplary instrument described here has a measurement module which has a capability to perform time-resolved fluorometry (TRF), prompt photoluminescence (FI), and absorbance (ABS) measurement modes. Additionally it may be possible to perform chemiluminescence measurements.

Figure 9A:
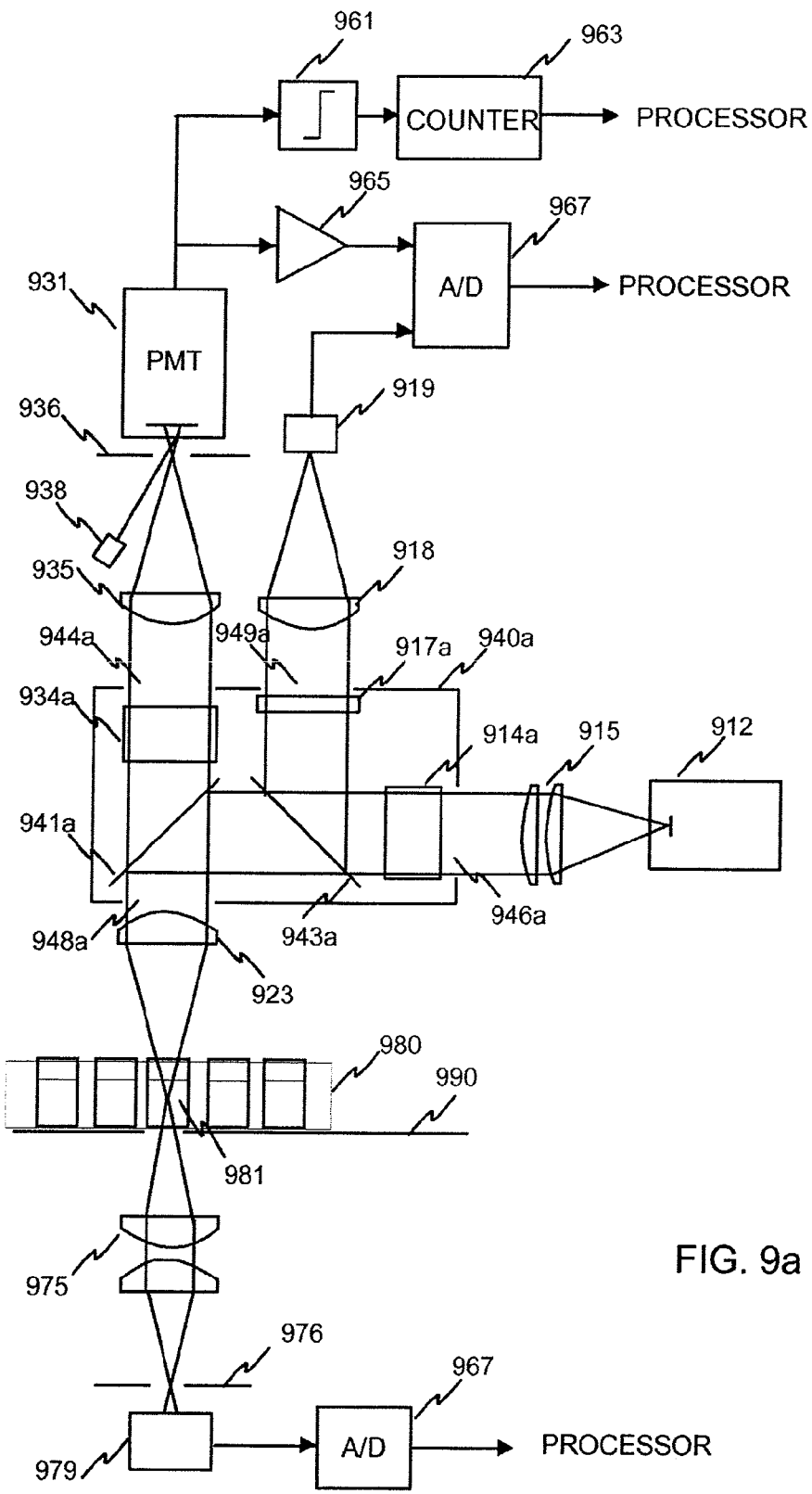
FIG. 9a illustrates main components used in photoluminescence measurement of an exemplary measurement unit.

FIG. 9a illustrates main components which are used for the optical measurement in TRF and FI modes of photoluminescence measurement. The instrument comprises an illumination source 912 for the excitation of a sample. The illumination source may be e.g. a flash lamp. The radiation from the illumination source 912 is collimated with lens 915 and directed to an optical module 940a. The lens 915 is preferably implemented as a double lens or aspheric lens. The light beam enters the optical module through an opening 946a at the wall of the optical module. The light beam is directed through an excitation filter 914a, which may be e.g. an interference filter. The excitation filter of the optical module is thus selected that it passes the wavelength which is used in the excitation of the label to be measured. The selectable optical modules are specific for certain labels and measurement modes and have therefore corresponding excitation filters.

In order to achieve a good accuracy of the intensity of the excitation beam it is possible to use a reference detector 919 for measuring the intensity of the excitation beam and for providing feedback for controlling the illumination source. The optical module has a beam splitter mirror 943a which reflects a small part of the light beam for the reference detector. The reflected light beam is filtered with a neutral density filter 917a and led through an opening of the optical module to a lens 918, which focuses the light beam to the active surface of the reference detector 919. The signal received from the reference detector is converted into digital signal in an analogue-digital converter 967 and led to the control circuitry of the instrument. The reference detector receives the excitation beam after the filtering at the excitation filter and therefore the reference detector measures the same wavelengths of the excitation beam which are effective in the excitation.

The excitation light beam which is transmitted through the beam splitter 943a is reflected by another mirror 941 a which may be a beam splitter mirror or a dichroic mirror. The reflected excitation beam is led through an opening 948a at the wall of the optical module to a lens 923, which focuses the excitation beam into a sample 981. There may optionally be an aperture between the lens 923 and the sample 981 for preventing the light beam from entering adjacent samples. The size of the aperture depends on the type of the sample plate under use. For example, the aperture for a sample plate with 384 sample wells is smaller than the aperture for a sample plate with 96 sample wells. The aperture may be controlled by applying apertures of different sized in a controllably movable slide.

The sample 981 resides in a sample well of a sample plate 980. The sample plate may be e.g. a microtitration plate with 96 or 384 sample wells. The sample plate is coupled to a conveyor 990 which can move the position of the sample plate in horizontal and possibly vertical directions. The conveyor moves the sample plate into positions where the samples to be measured are successively at the optical path of the measurement.

The photoluminescence emission beam from the sample 981 is directed to the lens 923, which collimates the emission beam. There may be an aperture 924 between the lens 923 and the sample 981 for preventing light entering from adjacent samples to the detector. The emission beam is led from the lens 923 through the opening 948a at the wall of the optical module and through the dichroic mirror 941 a. The dichroic mirror 941 a can be designed for certain labels so that it reflects the excitation wavelength but transmits emission wavelength. The mirror may alternatively be an ordinary beam splitter mirror, which reflects 50% of the beam intensity, and transmits 50% of the beam intensity. The mirror may also be based on polarization etc. A beam splitter mirror can be produced e.g. by forming reflective coating for the mirror to be e.g. stripes or dots, which cover only a part of the mirror surface.

The emission beam further transmits an emission filter 934 and an opening 944a at the wall of the optical module. The emission filter may be e.g. an interference filter. The emission filter of the optical module is thus selected that it passes the wavelength, which is emitted by the label to be measured. The selectable optical modules are specific for certain labels and measurement modes, and have therefore corresponding emission filters.

The emission beam is then focused with a lens 935 to and led through an aperture 936 to the active surface of a detector 931. The detector is preferably a photomultiplier tube (PMT). It is possible to have a fixed aperture at the input of the photomultiplier tube for measuring larger samples, such as a 96-well sample plate. For smaller samples, such as samples in a 384-well sample plate there can be an aperture slide 936 with selectable apertures, by which an aperture of suitable size can be selected.

The detector measures the intensity of the emission radiation received from the measurement volume of the sample. The output signal of the photomultiplier tube can be processed in two alternative ways. In analogue signal measurement the signal is amplified in an amplifier 965 and converted into digital form in an analogue-digital converter 967. The converted signal is then led to a processor of the control circuitry, which may calculate signal integral values over the reception time windows and determine measurement results based on the calculation. This type of signal processing measures the total current which is created at the photomultiplier tube as a result of the photons of the emission beam. It is useful at high intensities of emission beams when single pulses created by the photons cannot be detected separately. This type of signal processing is suitable for e.g. prompt photoluminescence measurement where emission intensities are generally high.

In another way to process the output signal of the photomultiplier tube the signal is led to a discriminator 961 which detects pulses created by single photons. These pulses are counted in the counter 963 over the periods of reception time windows. The counted values are led to a processor of the control circuitry. This type of signal processing measures the number of photons entered to the photomultiplier tube within a specified time period. It is useful when the intensity of the emission beam is low and the individual pulses created by photons can be counted separately. This type of signal processing is suitable for e.g. time-resolved fluorometry measurement where emission intensities are generally low. However, it is also possible to affect the intensity of the light beam which is entered to the photomultiplier tube. It is possible e.g. to make an initial measurement in order to check the emission activity of the sample. It is then possible to adjust the beam intensity entering the photomultiplier tube e.g. by controlling the intensity of the excitation light, by attenuating the emission beam with an attenuating filter or by adjusting the signal acquisition delay of the TRF measurement. This way it is possible to adjust the light beam entering the photomultiplier tube into a correct dynamic range. Instead of using an initial measurement it is also possible to estimate the activity of the sample on the basis of the assaying process and processing parameters.

The measurement results usually correspond to the amount of the measured substance within the measurement volume. The measurement result may be stored by the control circuitry of the instrument and displayed on the user interface of the instrument. The control circuitry for processing the measurement results may reside e.g. in the measurement unit of in the main control unit of the instrument.

The optical module 940a is installed on e.g. a controllable slide which preferably has specific optical modules for each measurement mode and label. The instrument selects an optical module to be used in each measurement on the basis of the selected measurement type. The control circuitry of the instrument then controls the movement of the slide in order to position the selected optical module into the optical path of the measurement. The optical modules include several optical components which are specific to measurement modes and labels. The optical modules may include dichroic or beam splitter mirror(s), optical filter(s), aperture(s) and openings for the light beams. When all measurement-specific optical components are included in the optical modules it is not necessary to provide other controlled slides or mechanisms for other selectable optical components. Such an arrangement also decreases risks of using wrong optical components in the measurement. It also reduces the need for calibration of the positions of the optical components and reduces the installation work of the optical components when, for example, the available measurement modes are changed or updated.

In one useful embodiment there is a specific first set of optical modules and analogue, cumulative signal detection used in prompt photoluminescence, and a specific second set of optical modules and pulse counting signal detection used in time-resolved fluorometry, wherein the second set of optical modules include different combinations of optical components compared to the first set of optical modules. This way it is possible to create optical paths and electronic processing which are separately optimised for both the prompt photoluminescence and the time-resolved fluorometry measurement modes.

FIG. 9a also shows a reference light source 938, such as a light emitting diode. The reference light source emits light directly to the input window of the photomultiplier tube 931. The reference light source can be used for calibrating the photomultiplier tube and the related electronics. The reference light source may be controlled to provide different light intensities for the calibration of the analogue detection and pulse detection circuitry.

FIG. 9a shows the photoluminescence measurements being performed from above the sample, but the measurements can alternatively be made from below the sample. It is also possible to apply excitation from above the sample and receiving the emission from below the sample, or vice versa.

The instrument of FIG. 9a is equipped with an illumination source and related components for providing excitation/activation of a sample, but the instrument is naturally also suitable for measurements which do not require excitation with light, such as chemiluminescence measurement. Chemiluminescence measurement can be performed with the same detector which is used in the photoluminescence measurement. However, the optical module can be without optical components for the excitation beam, and no filters are either required for the emission beam. However, a better sensitivity is achieved in the chemiluminescence measurement by using a separate detector. A chemiluminescence detector can be positioned close to the sample being measured because no optical components between the sample and the chemiluminescence are necessarily required.

FIG. 9a also shows optical components which are used for detecting a light beam which penetrates through the sample in absorbance measurements. The light beam which is emitted by the light source 912 and penetrates through the sample 981 is focused by a lens system 975 to the active surface of a photometric detector 979. An aperture 976 may be located between the lens system 975 and the detector 979. The output signal from the detector is converted into digital form in the analogue-digital converter 967, which may be the same converter used for photoluminescence measurements. The converted digital signal is further directed to a processor for the determination of absorbance.

The absorbance measurement may be performed for determining concentration of colourful label substances within the samples and for determining whether there is a sample disc in the sample well. In the absorbance measurement it is preferable to use an optical module which has optical components optimised for the absorbance measurement, possibly for a specific label. The determination of whether there is a sample disc in the sample well is possible to be performed with an optical module specific for the absorbance measurements. However, it is also possible to make the determination simultaneously or successively with the photoluminescence measurement using the optical module of the photoluminescence measurement.

Figure 9B:
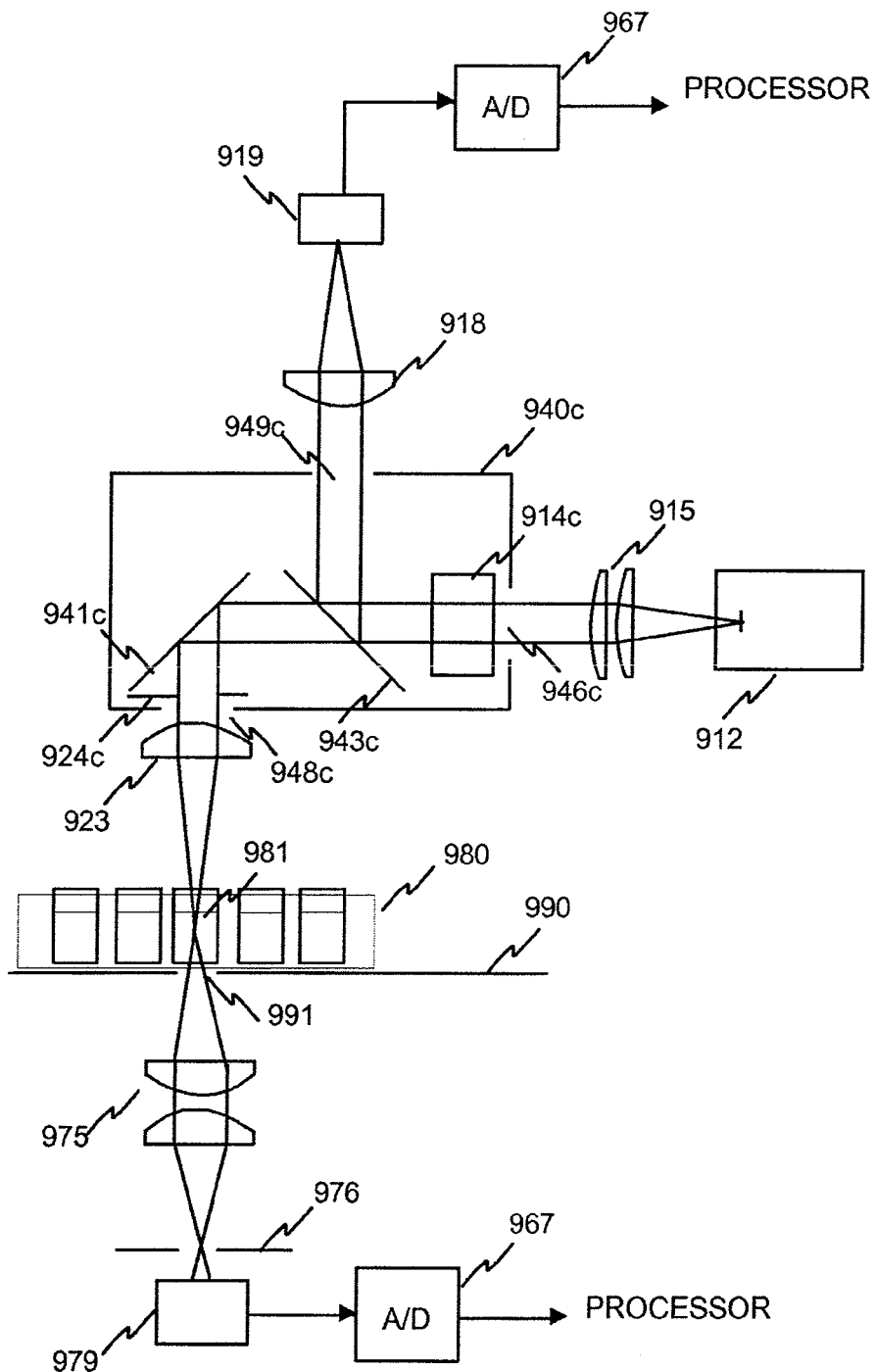
FIG. 9b illustrates main components used in absorbance measurement of an exemplary measurement unit.

FIG. 9b illustrates the components of an exemplary measurement unit which are used in photometric absorbance measurement when the optical module in use is specific for the absorbance measurement. The illumination source 912 is controlled to give one or several successive light pulses for the absorbance measurement. The illumination source may be the same lamp, such as a flash lamp, which is used for the photoluminescence measurements. The radiation from the illumination source 912 is collimated with lens 915 and directed to an optical module 940c, which is specific for the absorbance measurements. The light beam enters the optical module through an opening 946c at the wall of the optical module. The light beam is directed through an absorbance filter 914c. The absorbance filter of the optical module is thus selected that it passes the wavelength which is used in the specified absorbance measurement. It is also possible to make successive absorbance measurements on the same sample using filters of different wavelengths by changing the optical module between the measurements.

The reference detector 919 can also be used in the absorbance measurement for measuring the intensity of the light pulses and for providing feedback for controlling the illumination source. The optical module has a beam splitter mirror 943c which reflects a part of the light beam for the reference detector. The reflected light beam is led through an opening of the optical module to a lens 918, which focuses the light beam to the active surface of the reference detector 919. The signal received from the reference detector is converted into digital signal in an analogue-digital converter 967 and led to the control circuitry of the instrument.

The light beam which is transmitted through the beam splitter 943c is reflected by another mirror 941 c. The reflected light beam is led through an aperture 924c and an opening 948c at the wall of the optical module. The light beam is further focused by lens 923 into a sample 981 residing on a sample plate 980. After penetrating through the sample the light beam is led through an opening 991 of the platform 990 and focused with a lens system 975 to the active surface of the light detector 979. An aperture 976 may be provided between the lens system 975 and the detector 979. The detector may be a photodiode, for example. The signal received from the detector is led to the analogue-digital converter 967, and the converted digital information is further led to a processor for the determination of the measurement result.

The absorbance measurement can be made with one light pulse, but a more accurate measurement result is achieved by applying a plurality of light pulses, such as 100 pulses, and calculating the measurement result on the basis of the individual results. The final result may be e.g. an average value of the individual absorbance measurement results of the sample.

The detectors and light sources including their electronics are shown reduced in size compared to other components in FIGS. 9a and 9b. On the other hand, the other optical components and samples are shown relatively enlarged in Figures in order to better illustrate the optical paths in the instrument.

Other Functional Units

The exemplary instrument has a temperature control unit and an air dyer unit for controlling temperature and humidity inside the instrument. It is preferable that the air dryer unit controls primarily the air humidity within a plate storage unit. In many assays it is essential that during the storage of the samples, such as blood discs, the humidity does not exceed a predetermined limit. The temperature control may be implemented with e.g. one or several Peltier elements which can be controlled to either heat or cool the air inside the instrument. The temperature control unit preferably also has fans for circulating the air inside the instrument in order to reduce gradients of temperature and humidity within the instrument. The air dryer may also be implemented with a Peltier element which is cooled to condensate possible excessive humidity inside the instrument. The temperature unit and the air dryer unit have corresponding temperature and humidity sensors in order to control the temperature and humidity values in adjusted values.

Exemplary Assay Methods for Screening

Figure 10:
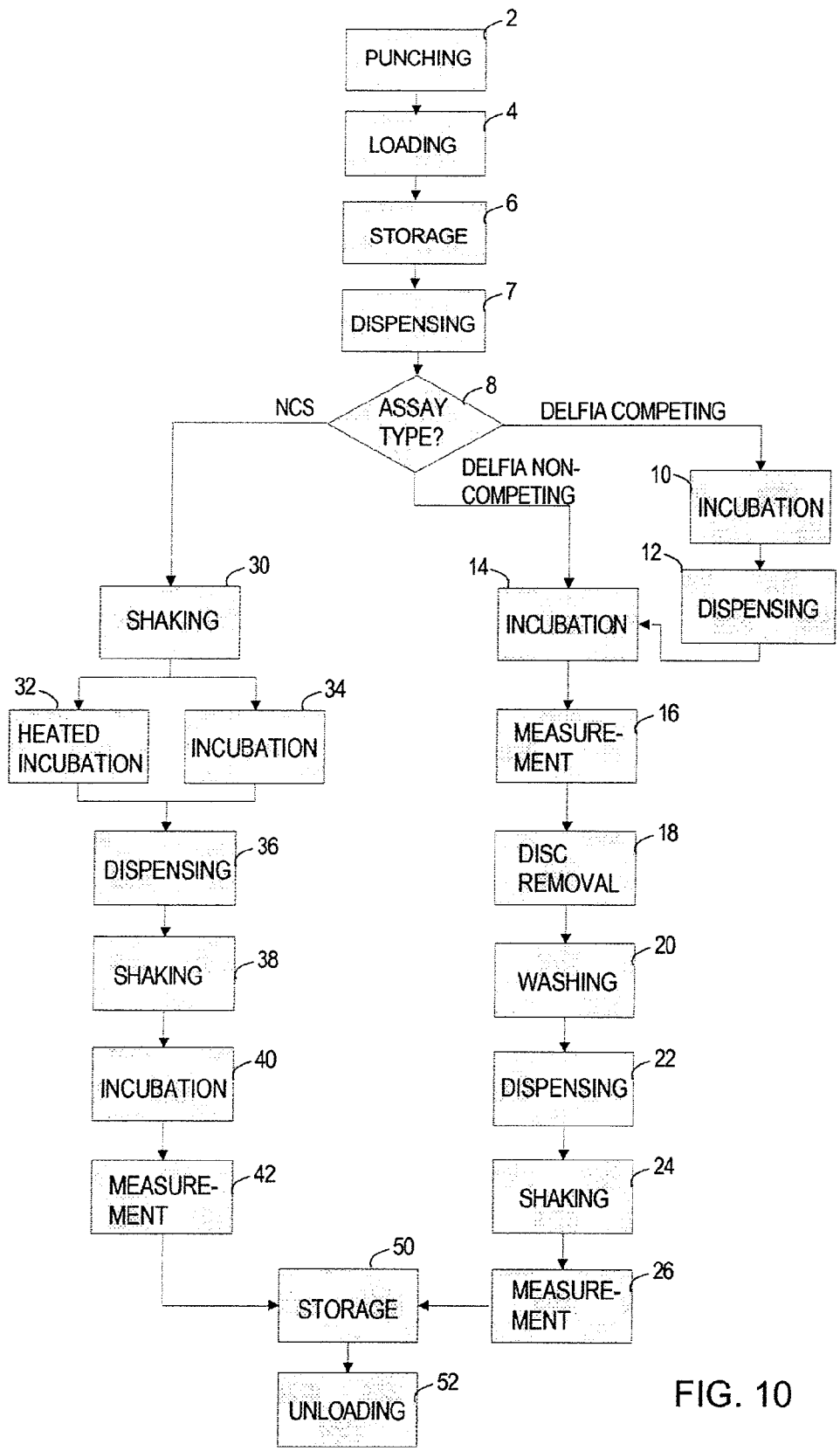
FIG. 10 illustrates a flow diagram of exemplary assaying methods.

FIG. 10 illustrates a flow diagram of an exemplary method for processing samples with an automated instrument. The method relates to assaying blood spots which are impregnated into a filter paper. First in phase 2 sample discs are punched from the filter papers. This may be performed with a separate punching tool. The sample discs may be of a diameter 1-4 mm, for example, such as 3,2 mm. The punched discs are set into sample wells of sample plates so that one sample well includes at most one disc. The sample plates are then loaded into an input stack of the instrument in phase 4. The manipulator of the instrument then transfers the sample plates to the plate storage module, phase 6. Next in phase 7 a sample plates is transferred to the dispensing module where reagent is dispensed to the sample wells. A suitable concentration can be achieved by dispensing the reagent with a small volume dispenser and dispensing buffer with a low volume dispenser.

The next phase depends on the determined type of assay, phase 8. The assay type is determined e.g. by reading a bar code of the sample plate when the sample plate is loaded into the instrument. In the illustrated case three types of assay processes with corresponding chemistries are available; Newborn Chemistry Screening assay, competing Delfia assay and non-competing Delfia assay. If a competing Delfia assay is selected the sample plate is first transferred to a shaker incubator module for shaking incubation, phase 10. The sample plate is incubated for a determined time in a temperature of e.g. 25° C. Next in phase 12 the sample plate is transferred to the dispensing module where reagent is dispensed to the sample wells. A suitable concentration can be achieved by dispensing the reagent with a low volume dispenser and dispensing buffer with a large volume dispenser.

Next the sample plates are transferred to a shaker incubation module for shaking incubation in phase 14. The samples are incubated for a determined time in a temperature of e.g. 25° C. If non-competing Delfia assay is selected in phase 8 the phase 14 is implemented directly without performing phases 10 and 12. The further phases are the same for both competing and non-competing assays.

Next in phase 16 the sample plate is transferred to the measuring module.

In phase 18 the sample plate is transferred to the disc remover module where sample discs are removed from the sample wells. After the disc removal the sample plate is transferred to the wash module where sample wells are washed and loose substances are thus removed from the sample well, phase 20.

Next in phase 22 the sample plate is transferred to the bulk reagent dispensing module where measuring liquid is dispensed to the sample wells of the sample plate. Thereafter the sample plate is transferred to the shaker incubator for shaking of the sample plate, phase 24. After the shaking the sample plate is transferred to the measurement module where the analyte is measured with time-resolved fluorometry measurement in phase 26.

After the measurement the sample plate is transferred to the plate storage in phase 50. When the user wants to unload the sample plate from the instrument the sample plate is transferred from the plate storage to the output stacker.

If in phase 8 Newborn Chemistry System (NCS) assay is selected the sample plate is transferred to a shaker module next after the phase 8. The sample plate is shaken for a determined time in the shaker module, phase 30. After the shaking the sample plate is transferred to a heating incubator or to a room temperature incubator, depending on the selected process. If a room temperature incubation is selected the incubation may take place in a shaker incubation module or in a plate storage module. The sample plate is then incubated for a determined time, phase 32 or 34.

Next in phase 36 the sample plate is transferred to a dispenser module or a bulk reagent dispensing module where liquid is dispensed to the sample wells of the sample plate for interrupting the reaction. Thereafter the sample plate is transferred to the shaker incubator for shaking of the sample plate, phase 38. The sample plate is then transferred to a plate storage wherein the sample plate is incubated for a determined time, phase 40.

Next in phase 42 the sample plate is transferred to the measuring module. In phase 42 the analytes in the sample wells are also measured with prompt photoluminescence (FI) measurement in the measuring module.

After the measurement the sample plate is transferred to the plate storage in phase 50. When the user wants to unload the sample plate from the instrument the sample plate is transferred from the plate storage to the output stacker.

The above description of the assaying methods shows that different methods may include similar and different processing phases in partly same and partly different succession. For example, incubation may be required in room temperature or elevated temperature, non-shaking or shaking mode, with continuous or interval shaking. Also the incubation times may be different. The phases for dispensing reagents to sample wells may also be different regarding the dispensed substances and volumes as well as the instants of the dispensing phases within the processing schedule. The possible phase(s) of removing substance from the sample wells may also be different.

The present invention allows simultaneous processing of several sample plates. Several sample plates can be processed simultaneously in a same processing unit. It is also possible to process sample plates simultaneously in different processing units. Further, it is possible to process or store a plurality of sample plates simultaneously in at least two processing or storage units. It is further possible to perform optical measurements of different modes for same or different samples. Further, the invention allows the transferring of the sample plates between the processing and storing units independently of the ongoing processes in other units.

In this patent specification the structure of the components in an optical measurement instrument or details of assay processes are not described in more detail as they can be implemented using the description above and the general knowledge of a person skilled in the art.

Above, only some embodiments of the solution according to the invention have been described. The principle according to the invention can naturally be modified within the frame of the scope defined by the claims, for example, by modification of the details of the implementation and ranges of use.

For example, the described exemplary instrument has processing and storage modules on four sides of a base frame structure. However, in is naturally possible to install modules into numerous alternative assemblies. Although it is advantageous to have modules installed in four stacks, there they may also be installed in other number of stacks, they can be installed in a totally horizontal constellation or in a combination of those.

Also, certain optical measurement modes and assay processes have been described above. However, it is natural that the invention can be applied to other alternative measurement modes currently existing or to be developed in future.

Also, although the invention has been described with reference to microtitration plates of rectangular shape it is equally applicable to any form of sample matrixes or single sample wells.

In addition to the invention defined by the independent claims, this specification includes several features and which may also be further inventions or parts of further inventions. Therefore, any combination of features or devices disclosed in the above description or in the appended claims may be regarded as an additional independent invention, and any such combination can be a basis for a divisional application.

The invention claimed is:

1. An automated, self-contained instrument for assaying and measuring of samples, wherein the samples are sample discs impregnated with blood and located in wells of sample plates, the instrument comprising:
   (a) at least 4 vertical frames in adjacent pairs forming a frame structure;
   (b) a turnable manipulator located inside the frame structure for transferring sample plates in three orthogonal directions or combinations thereof;
   (c) a plurality of units for processing or storing sample plates, the units being installed on and outside the frame structure and adjacent to said turnable manipulator in order to be accessible by the turnable manipulator, said units comprising:
      (i) at least one dispensing unit for dispensing reagents or other assay components to the sample wells,
      (ii) at least two units for simultaneously processing or storing a plurality of sample plates,
      (iii) at least one unit for removing substance from the sample wells, and
      (iv) one or several measurement units, the measurement unit(s) providing a capability for the instrument to optically measure samples in at least two measurement modes,
      wherein the turnable manipulator is configured to turn by at least 270 degrees in relation to a vertical axis in order to transfer sample plates between all units installed on the frame structure.

2. The instrument according to claim 1, wherein at least one unit for processing or storing sample plates is a module which is designed to allow installation and removal as a whole to/from the instrument.

3. The instrument according to claim 2, wherein the module comprises a front panel having a positioning means to position the module in relation to a location for a sample plate in the module, the front panel being arranged in a stationary position with respect to the turnable manipulator for positioning the module with respect to the frame structure.

4. The instrument according to claim 3, wherein the position of the front panel with respect to the turnable manipulator is adjustable at least in the horizontal plane for allowing exact mutual positioning of the front panel and the turnable manipulator.

5. The instrument according to claim 3, wherein the front panel is designed to significantly contribute to the rigidity of a structure supporting the turnable manipulator.

6. The instrument according to claim 3, wherein the turnable manipulator and the frame structure, and optionally the front panel(s), form an integral unit.

7. The instrument according to claim 1, wherein a module can be installed in alternative positions within the frame structure, whereby the information on the locations of the modules is stored in the system for controlling the movements of the turnable manipulator.

8. The instrument according to claim 1, further comprising at least one plate holder for receiving and holding a sample plate.

9. The instrument according to claim 1, wherein the at least two units for simultaneously processing or storing a plurality of sample plates comprise at least two incubator units which are arranged to provide simultaneous processing in different processing modes.

10. The instrument according to claim 1, wherein the at least one unit for removing substance from the sample wells is a washing unit for washing the wells of the sample plates.

11. The instrument according to claim 1, wherein the at least one unit for removing substance from the sample wells is a disc remover unit for removing a sample disc from a sample well.

12. The instrument according to claim 1, wherein the instrument comprises an air dryer for controlling the humidity of the air within the instrument and within a plate storage unit, wherein the air dryer comprises controlling means for controlling the humidity of the air into a humidity value that is adjustable within a determined range.

13. A method for assaying and measuring of blood samples in the automated self-contained instrument of claim 1, wherein the samples are impregnated into sample discs and located in wells of sample plates, and the method comprises phases in which a sample plate is processed in the plurality of processing units installed on the frame structure and the sample plate is moved between the units for processing or storing by the turnable manipulator located inside the frame structure, the method comprising phases in which:

reagents or other assay components are dispensed to the sample wells, a plurality of sample plates are simultaneously processed or stored in at least two units, substance is removed from the sample wells, samples are optically measured in at least two measurement modes, and the sample plates are moved by the turnable manipulator in three orthogonal directions or combinations thereof including being rotated by the turnable manipulator by at 270 degrees inrelation to a vertical axis to transfer the sample plates between the processing units.

14. The method according to claim 13, wherein the at least one unit for processing or storing sample plates is installed or removed as a whole module to/from the instrument, the module being positioned on the instrument with positioning means, wherein the positioning means are accurately positioned in a front panel of the module in relation to the location for a sample plate in the module, thereby allowing a change of a module without individual calibration of the mechanical interface between the turnable manipulator and the module.

* * * * *